US012620465B2

(12) United States Patent　　　　(10) Patent No.:　US 12,620,465 B2

Hiasa　　　　　　　　　　　　　　　　(45) Date of Patent:　　　May 5, 2026

(54) LEARNING APPARATUS, LEARNING METHOD, TRAINED MODEL, AND PROGRAM

(71) Applicant: FUJIFILM Corporation, Tokyo (JP)

(72) Inventor: Yuta Hiasa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 319 days.

(21) Appl. No.: 18/357,143

(22) Filed: Jul. 23, 2023

(65) Prior Publication Data

US 2023/0368880 A1　　　Nov. 16, 2023

Related U.S. Application Data

(63) Continuation of application No. PCT/JP2022/001350, filed on Jan. 17, 2022.

(30) Foreign Application Priority Data

Jan. 26, 2021　　(JP) ................................. 2021-010381

(51) Int. Cl.
　　*G06V 10/774*　　　(2022.01)
　　*G06T 7/00*　　　　(2017.01)
　　*G16H 15/00*　　　(2018.01)
(52) U.S. Cl.
　　CPC ........... *G16H 15/00* (2018.01); *G06T 7/0012* (2013.01); *G06V 10/774* (2022.01);
　　　　　　　(Continued)
(58) Field of Classification Search
　　None
　　See application file for complete search history.

(56) References Cited

U.S. PATENT DOCUMENTS 10,790,056 B1 *　9/2020　Accomazzi ............ G16H 30/20
11,468,659 B2 *　10/2022　Ichinose ................ G16H 50/70
　　　　　　　　　(Continued)

FOREIGN PATENT DOCUMENTS

CN　　111223085　　6/2020
CN　　112215845　　1/2021
JP　　2019153250　　9/2019

OTHER PUBLICATIONS

Jianbo Yuan et al., "Automatic Radiology Report Generation based on Multi-view Image Fusion and Medical Concept Enrichment", retrieved from arXiv database, arXiv:1907.09085v2 [eess.IV], Jul. 23, 2019, pp. 1-9.

(Continued)

*Primary Examiner* — Tsung Yin Tsai
(74) *Attorney, Agent, or Firm* — JCIPRNET

(57)　　　　　　ABSTRACT

The learning apparatus includes a processor (129), a memory (114), and a learning model (126). The processor (129) performs processing of inputting a pseudo simple X-ray image (204), which is generated by projecting an X-ray CT image (202), to the learning model (126), processing of generating a second interpretation report (208) with respect to the pseudo simple X-ray image (204) by converting a first interpretation report (206), processing of acquiring an error between an estimation report (210) with respect to the pseudo simple X-ray image (204) output by the learning model (126) on the basis of the input pseudo simple X-ray image (204), and the second interpretation report (208), and processing of training the learning model (126) by using the error.

15 Claims, 22 Drawing Sheets

(52) U.S. Cl.

CPC .............. *G06T 2207/10081* (2013.01); *G06T 2207/20081* (2013.01); *G06V 2201/031* (2022.01); *G06V 2201/12* (2022.01)

(56) References Cited

U.S. PATENT DOCUMENTS

| | | | | |
|---|---|---|---|---|
| 11,978,273 | B1 * | 5/2024 | Ramaswamy | ....... G06V 30/412 |
| 11,984,206 | B2 * | 5/2024 | McKinney | ............... G06N 3/08 |
| 2019/0279751 | A1 * | 9/2019 | Nakamura | ............. G16H 30/40 |
| 2019/0341150 | A1 * | 11/2019 | Mostofi | .................. G16H 50/20 |
| 2020/0105414 | A1 * | 4/2020 | Kikuchi | ............... G06N 3/0464 |
| 2020/0321101 | A1 | 10/2020 | Karargyris et al. | |
| 2020/0334416 | A1 * | 10/2020 | Vianu | .................. G06N 3/0442 |
| 2020/0334566 | A1 * | 10/2020 | Vianu | .................... G16H 50/70 |
| 2020/0334809 | A1 * | 10/2020 | Vianu | .................. G06V 30/333 |
| 2020/0335199 | A1 * | 10/2020 | Accomazzi | ............ G16H 30/20 |
| 2020/0387729 | A1 * | 12/2020 | Ichinose | .................... G06T 7/11 |
| 2021/0065859 | A1 * | 3/2021 | McKinney | ............. G16H 15/00 |
| 2021/0326939 | A1 * | 10/2021 | Navar | ................ G06Q 20/4016 |
| 2023/0022549 | A1 * | 1/2023 | Fuchigami | ................ G06T 7/12 |
| 2023/0377153 | A1 * | 11/2023 | Hennersperger | ..... G06V 10/774 |
| 2024/0127613 | A1 * | 4/2024 | Hiasa | ....................... A61B 6/03 |
| 2024/0152706 | A1 * | 5/2024 | De Vrieze | ................ G06N 3/02 |
| 2025/0157242 | A1 * | 5/2025 | Ramaswamy | ....... G06V 30/412 |

OTHER PUBLICATIONS

Christy Y. Li et al., "Knowledge-Driven Encode, Retrieve, Paraphrase for Medical Image Report Generation", The Thirty-Third AAAI Conference on Artificial Intelligence (AAAI-19), Jan. 27-Feb. 1, 2019, pp. 6666-6673.

Tomoko Ohkuma, "The Fujifilm Group's thinking on the future of imaging report systems", Innerversion, Feb. 25, 2020, with English abstract, pp. 60-61, vol. 35, No. 3.

Toru Nishino et al., "Using deep reinforcement learning with disproportionate characteristics to generate imaging reports", Proceedings of the Twenty-sixth Annual Meeting of the Association for Natural Language Processing, Mar. 9, 2020, with English abstract, pp. 201-204.

"International Search Report (Form PCT/ISA/210) of PCT/JP2022/001350", mailed on Apr. 19, 2022, with English translation thereof, pp. 1-7.

"Written Opinion of the International Searching Authority (Form PCT/ISA/237) of PCT/ JP2022/001350", mailed on Apr. 19, 2022, with English translation thereof, pp. 1-6.

* cited by examiner

Figure 3:
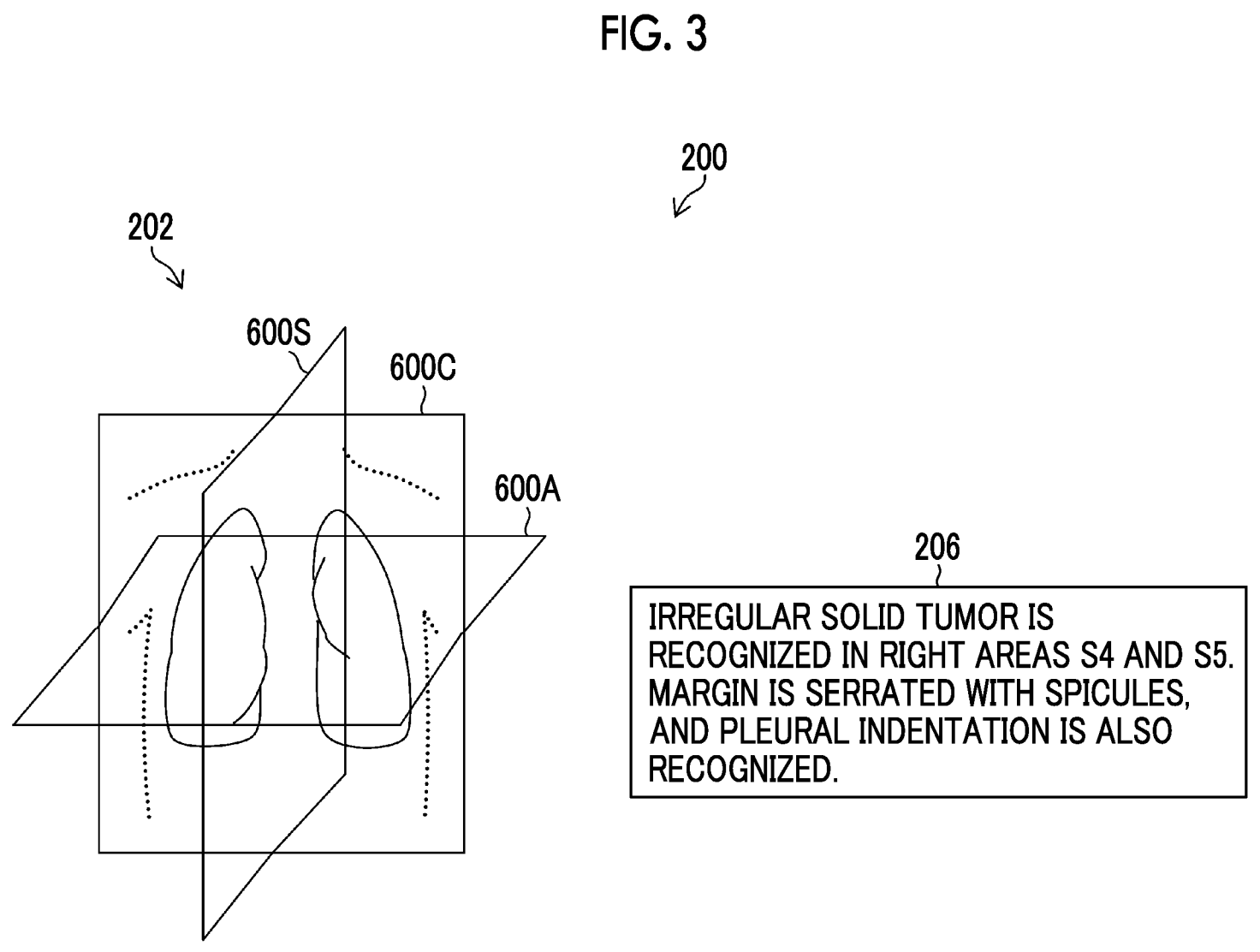

IRREGULAR SOLID TUMOR IS
RECOGNIZED IN RIGHT AREAS S4 AND S5.
MARGIN IS SERRATED WITH SPICULES,
AND PLEURAL INDENTATION IS ALSO
RECOGNIZED.

Figure 5:
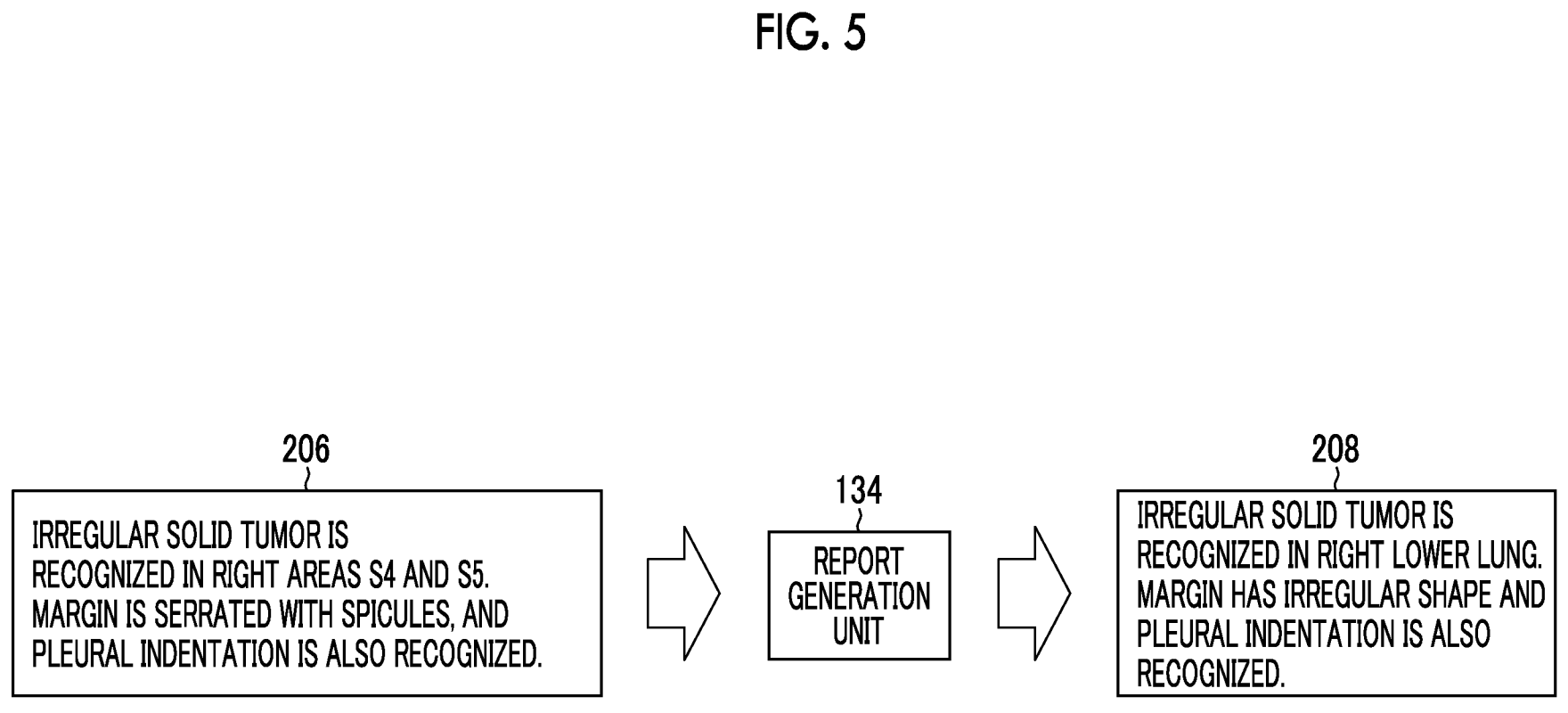

IRREGULAR SOLID TUMOR IS RECOGNIZED IN RIGHT LOWER LUNG. MARGIN HAS IRREGULAR SHAPE AND PLEURAL INDENTATION IS ALSO RECOGNIZED.

134

REPORT GENERATION UNIT

206

IRREGULAR SOLID TUMOR IS RECOGNIZED IN RIGHT AREAS S4 AND S5. MARGIN IS SERRATED WITH SPICULES, AND PLEURAL INDENTATION IS ALSO RECOGNIZED.

| THREE DIMENSIONAL ORGAN LABEL | TWO DIMENSIONAL ORGAN LABEL |
|---|---|
| RIGHT LUNG AREA S1 | RIGHT UPPER LUNG T1 |
| RIGHT LUNG AREA S2 | |
| RIGHT LUNG AREA S3 | |
| RIGHT LUNG AREA S4 | RIGHT LOWER LUNG T3 |
| RIGHT LUNG AREA S5 | |
| RIGHT LUNG AREA S6 | |
| RIGHT LUNG AREA S7 | RIGHT MIDDLE LUNG T2 |
| RIGHT LUNG AREA S8 | |
| RIGHT LUNG AREA S9 | |
| RIGHT LUNG AREA S10 | |

| THREE DIMENSIONAL DISEASE LABEL | TWO DIMENSIONAL DISEASE LABEL |
|---|---|
| SPICULE | IRREGULAR SHAPE |
| SERRATION | |
| LOBULATION | |
| CALCIFICATION | OO |
| CAVITY | X X |
| . . . | . . . |

FIG. 10

FIG. 15
260
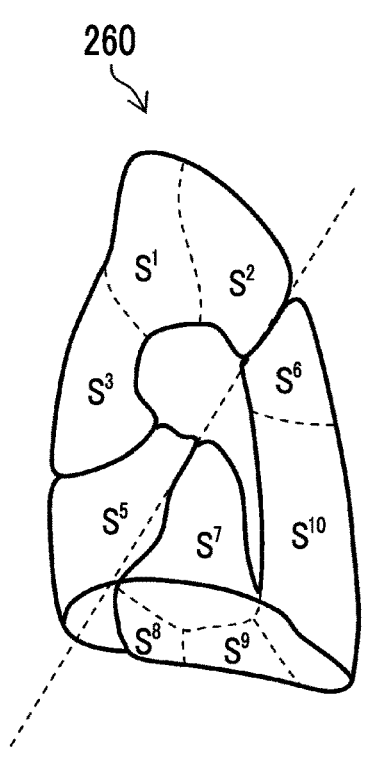
262
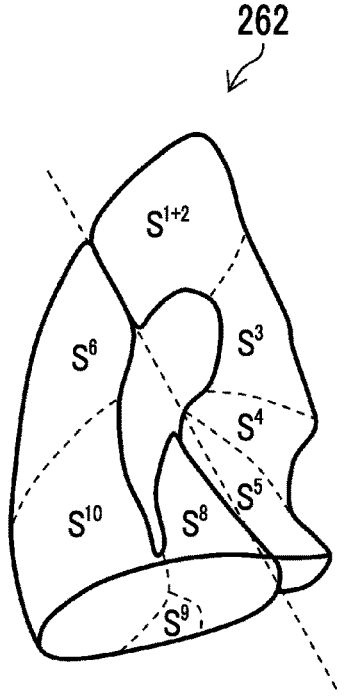
FIG. 16
264
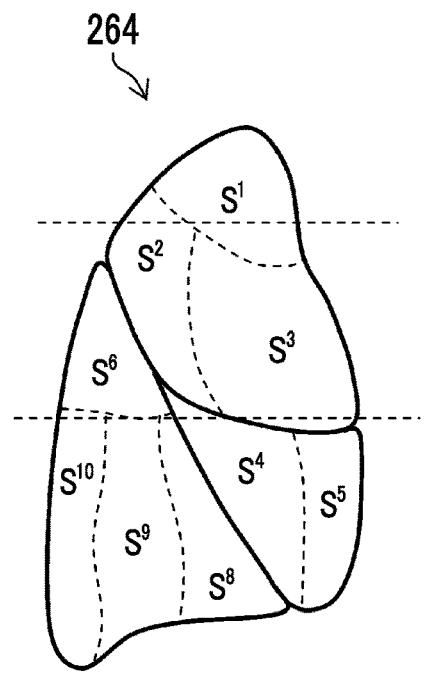
266
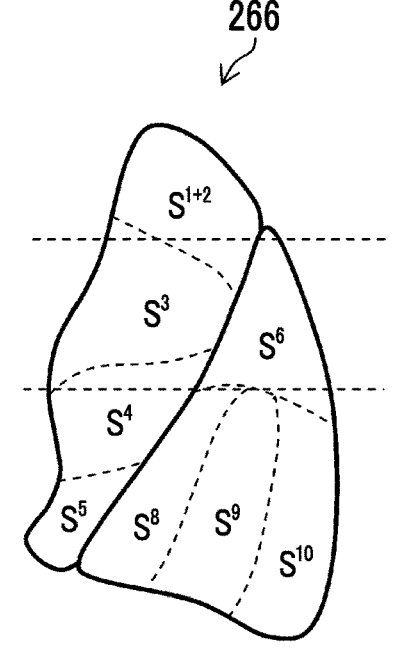

FIG. 17
268a
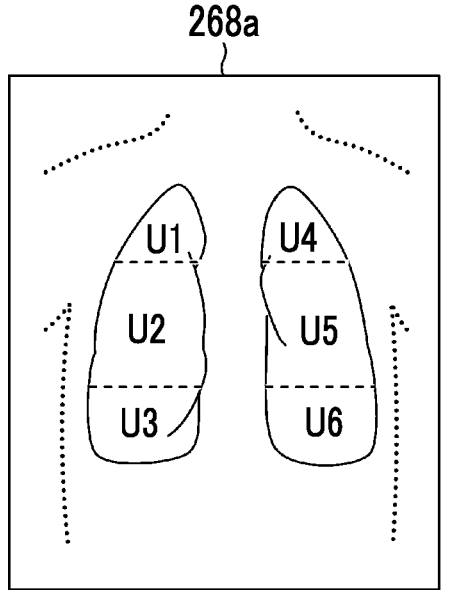
268b
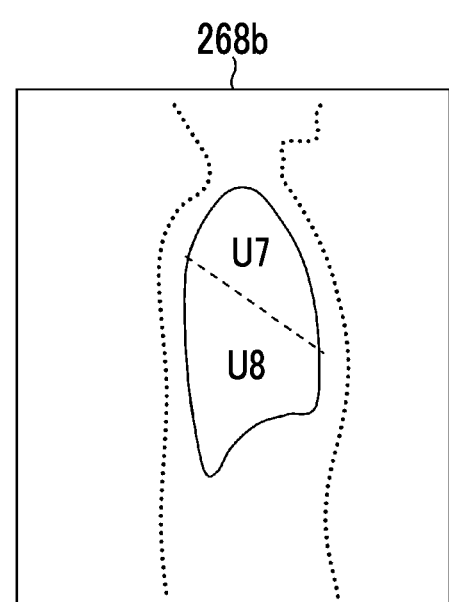

Figure 18:
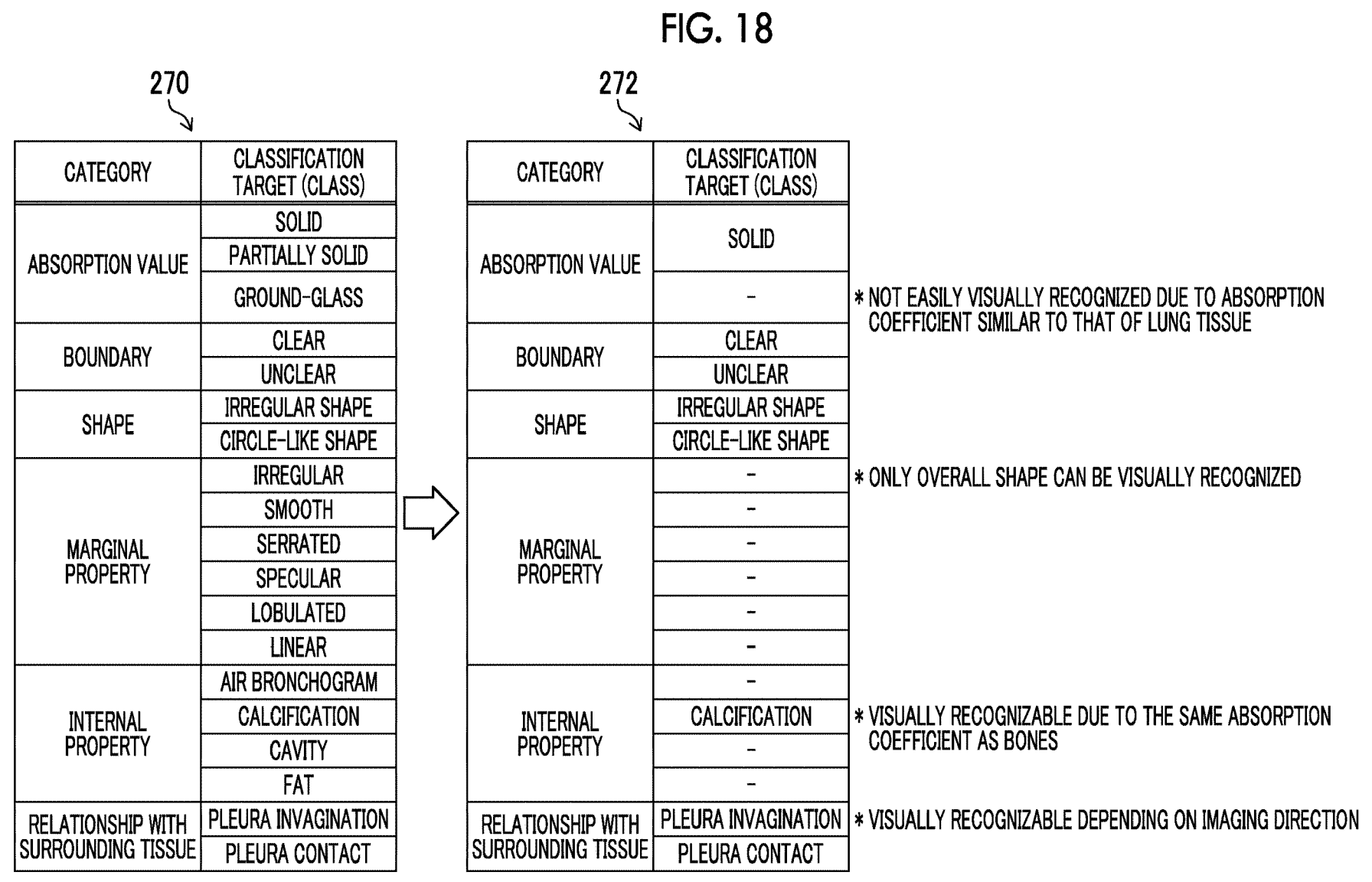

| CATEGORY | CLASSIFICATION TARGET (CLASS) |
|---|---|
| ABSORPTION VALUE | SOLID |
| | PARTIALLY SOLID |
| | GROUND-GLASS |
| BOUNDARY | CLEAR |
| | UNCLEAR |
| SHAPE | IRREGULAR SHAPE |
| | CIRCLE-LIKE SHAPE |
| MARGINAL PROPERTY | IRREGULAR |
| | SMOOTH |
| | SERRATED |
| | SPECULAR |
| | LOBULATED |
| | LINEAR |
| INTERNAL PROPERTY | AIR BRONCHOGRAM |
| | CALCIFICATION |
| | CAVITY |
| | FAT |
| RELATIONSHIP WITH SURROUNDING TISSUE | PLEURA INVAGINATION |
| | PLEURA CONTACT |

272

| CATEGORY | CLASSIFICATION TARGET (CLASS) | |
|---|---|---|
| ABSORPTION VALUE | SOLID | |
| | – | * NOT EASILY VISUALLY RECOGNIZED DUE TO ABSORPTION COEFFICIENT SIMILAR TO THAT OF LUNG TISSUE |
| BOUNDARY | CLEAR | |
| | UNCLEAR | |
| SHAPE | IRREGULAR SHAPE | |
| | CIRCLE-LIKE SHAPE | |
| MARGINAL PROPERTY | – | * ONLY OVERALL SHAPE CAN BE VISUALLY RECOGNIZED |
| | – | |
| | – | |
| | – | |
| | – | |
| | – | |
| INTERNAL PROPERTY | – | |
| | CALCIFICATION | * VISUALLY RECOGNIZABLE DUE TO THE SAME ABSORPTION COEFFICIENT AS BONES |
| | – | |
| | – | |
| RELATIONSHIP WITH SURROUNDING TISSUE | PLEURA INVAGINATION | * VISUALLY RECOGNIZABLE DEPENDING ON IMAGING DIRECTION |
| | PLEURA CONTACT | |

300

302

304

DISEASE LABEL

INTERPRETATION REPORT

SOLID TUMOR IS RECOGNIZED IN RIGHT LOWER LUNG.

FIG. 23

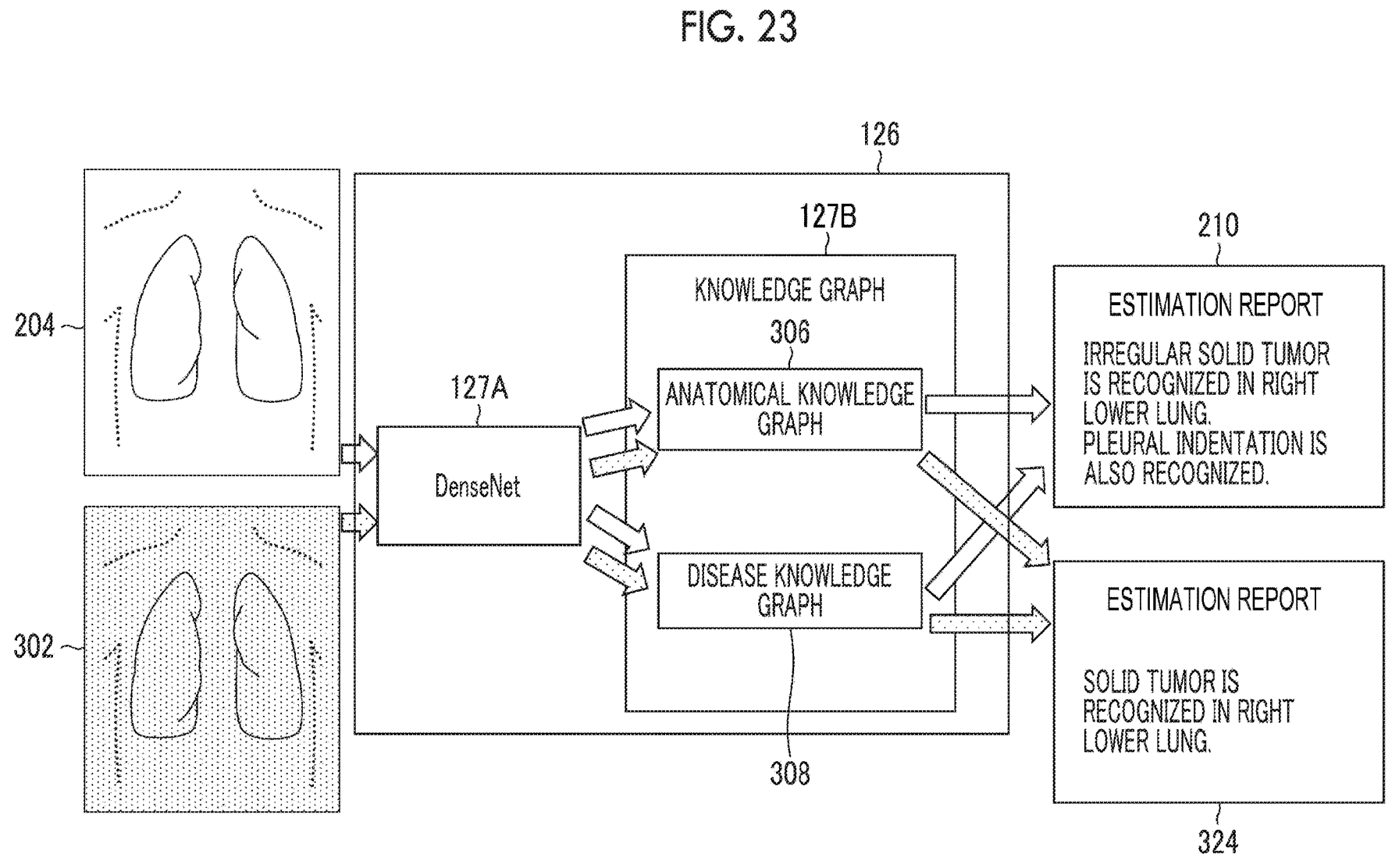

ESTIMATION REPORT

IRREGULAR SOLID TUMOR IS RECOGNIZED IN RIGHT LOWER LUNG. PLEURAL INDENTATION IS ALSO RECOGNIZED.

210

ESTIMATION REPORT

SOLID TUMOR IS RECOGNIZED IN RIGHT LOWER LUNG.

324

126

127B

KNOWLEDGE GRAPH

306

ANATOMICAL KNOWLEDGE GRAPH

DISEASE KNOWLEDGE GRAPH

308

127A

DenseNet

204

302

LEARNING APPARATUS, LEARNING METHOD, TRAINED MODEL, AND PROGRAM

CROSS-REFERENCE TO RELATED APPLICATIONS

The present application is a Continuation of PCT International Application No. PCT/JP2022/001350 filed on Jan. 17, 2022 claiming priority under 35 U.S.C § 119(a) to Japanese Patent Application No. 2021-010381 filed on Jan. 26, 2021. Each of the above applications is hereby expressly incorporated by reference, in its entirety, into the present application.

BACKGROUND OF THE INVENTION

1. Field of the Invention

The present invention relates to a learning apparatus, a learning method, a trained model, and a program, and particularly to a learning apparatus, a learning method, a trained model, and a program that perform learning regarding output of an interpretation report.

2. Description of the Related Art

In the related art, a disease or the like has been interpreted from a simple X-ray image by doctors or others, and interpretation results have been compiled into an interpretation report. However, interpretation of the simple X-ray image is not easy, even for a doctor, and the accuracy of the interpretation report may be low. Here, the simple X-ray image is a two dimensional image obtained by emitting X-rays and capturing a shadow on a plane.

In recent years, a trained model, which has been trained to output an interpretation report with respect to an input of a simple X-ray image using a machine learning technique, has been proposed.

For example, Yuan, Jianbo, et al., "Automatic radiology report generation based on multi-view image fusion and medical concept enrichment.", MICCAI, 2019 and Li, Christy Y., et al. "Knowledge-driven encode, retrieve, paraphrase for medical image report generation.", AAAI, 2019 describe a technique related to machine learning in which a chest X-ray image (simple X-ray image) is input and an interpretation report is output.

SUMMARY OF THE INVENTION

Here, in the techniques described in Yuan, Jianbo, et al., "Automatic radiology report generation based on multi-view image fusion and medical concept enrichment.", MICCAI, 2019 and Li, Christy Y., et al. "Knowledge-driven encode, retrieve, paraphrase for medical image report generation.", AAAI, 2019, a simple X-ray image having two dimensional information and an interpretation report thereof are used as training data. As described above, creation of the interpretation report of the simple X-ray image is not easy, even for a doctor, and the accuracy of the interpretation report may be low. One of the reasons for this is that since organs or the like originally having a three dimensional shape are shown as a two dimensional image in the simple X-ray image, the organs may be shown in an overlapping manner, or the original shape of the organs may be difficult to grasp. In addition, a trained model that has been trained by using such an interpretation report with low accuracy may not be able to output an interpretation report with high accuracy.

The present invention has been made in view of such circumstances, and an object of the present invention is to provide a learning apparatus, a learning method, and a program for generating a trained model that outputs an interpretation report with high accuracy by using high-quality training data with high accuracy, and a trained model trained by the learning method.

According to an aspect of the present invention for achieving the object, there is provided a learning apparatus comprising a processor, a memory that stores a training data set of an X-ray CT image having three dimensional information and a first interpretation report with respect to the X-ray CT image, and a learning model that generates an interpretation report from a simple X-ray image having two dimensional information, in which the processor performs processing of inputting a pseudo simple X-ray image, which is generated by projecting the X-ray CT image, to the learning model, processing of generating a second interpretation report with respect to the pseudo simple X-ray image by converting the first interpretation report, processing of acquiring an error between an estimation report with respect to the pseudo simple X-ray image output by the learning model on the basis of the input pseudo simple X-ray image, and the second interpretation report, and processing of training the learning model by using the error.

According to the aspect, the pseudo simple X-ray image and the second interpretation report with respect to the pseudo simple X-ray image are generated from the training data set of the X-ray CT image having three dimensional information and the first interpretation report with respect to the X-ray CT image, and learning is performed by using the pseudo simple X-ray image and the second interpretation report. Accordingly, in the aspect, since learning is performed using the pseudo X-ray image and the second interpretation report based on the X-ray CT image having a large amount of information and the first interpretation report, learning can be performed such that an interpretation report with high accuracy is output.

Preferably, in the processing of generating the second interpretation report, the second interpretation report is generated from the first interpretation report by converting an organ label included in the first interpretation report into an organ label of the second interpretation report.

Preferably, in the processing of generating the second interpretation report, the second interpretation report is generated from the first interpretation report by converting a disease label included in the first interpretation report into a disease label of the second interpretation report.

Preferably, in the processing of generating the second interpretation report, a first knowledge graph corresponding to the first interpretation report is converted into a second knowledge graph corresponding to the second interpretation report, and the second interpretation report is generated on the basis of the conversion.

Preferably, in a case in which the memory stores the X-ray CT image obtained by imaging a subject in a first posture and the learning model generates an interpretation report from the simple X-ray image obtained by imaging the subject in a second posture, in the processing of inputting the pseudo simple X-ray image, the pseudo simple X-ray image in the second posture is generated from the X-ray CT image in the first posture, and the pseudo simple X-ray image in the second posture is input to the learning model.

Preferably, in the processing of inputting the pseudo simple X-ray image, the pseudo simple X-ray image projected in a first direction and the pseudo simple X-ray image projected in a second direction are generated from the X-ray CT image, and the pseudo simple X-ray image projected in the first direction and the pseudo simple X-ray image projected in the second direction are input to the learning model.

Preferably, the memory stores an additional training data set of the simple X-ray image and a disease label of the simple X-ray image, and in the processing of acquiring the error, an error between the estimation report with respect to the pseudo simple X-ray image output by the learning model with reference to the disease label, and the second interpretation report is acquired.

Preferably, the memory stores an additional training data set of the simple X-ray image and a third interpretation report with respect to the simple X-ray image, and in the processing of acquiring the error, the error between the estimation report with respect to the pseudo simple X-ray image output by the learning model on the basis of the input pseudo simple X-ray image, and the second interpretation report and an error between an estimation report with respect to the simple X-ray image output by the learning model on the basis of the input simple X-ray image, and the third interpretation report are acquired.

In a learning method according to another aspect of the present invention, a processor trains a learning model, which generates an interpretation report from a simple X-ray image having two dimensional information, by using a training data set of an X-ray CT image having three dimensional information and a first interpretation report with respect to the X-ray CT image stored in a memory and the learning method comprises a step of inputting a pseudo simple X-ray image, which is generated by projecting the X-ray CT image, to the learning model, a step of generating a second interpretation report with respect to the pseudo simple X-ray image by converting the first interpretation report, a step of acquiring an error between an estimation report with respect to the pseudo simple X-ray image output by the learning model on the basis of the input pseudo simple X-ray image, and the second interpretation report, and a step of training the learning model by using the error.

Preferably, in the step of generating the second interpretation report, the second interpretation report is generated from the first interpretation report by converting an organ label included in the first interpretation report into an organ label of the second interpretation report.

Preferably, in the step of generating the second interpretation report, the second interpretation report is generated from the first interpretation report by converting a disease label included in the first interpretation report into a disease label of the second interpretation report.

Preferably, in the step of generating the second interpretation report, a first knowledge graph corresponding to the first interpretation report is converted into a second knowledge graph corresponding to the second interpretation report, and the second interpretation report is generated on the basis of the conversion.

A learning program according to another aspect of the present invention causes the processor to execute processing of each step in the above-described learning method.

A trained model according to another aspect of the present invention is trained by the above-described learning method.

According to the present invention, the pseudo simple X-ray image and the second interpretation report with respect to the pseudo simple X-ray image are generated from the training data set of the X-ray CT image having three dimensional information and the first interpretation report with respect to the X-ray CT image and learning is performed by using the pseudo simple X-ray image and the second interpretation report. That is, learning is performed using the pseudo X-ray image and the second interpretation report based on the X-ray CT image having a large amount of information and the first interpretation report, and thus learning can be performed such that an interpretation report with high accuracy is output.

BRIEF DESCRIPTION OF THE DRAWINGS

FIG. 3 is a diagram illustrating an X-ray CT image and a first interpretation report, which are an example of a training data set.

FIG. 4 is a diagram illustrating a pseudo image generation unit.

FIG. 5 is a diagram illustrating a report generation unit.

FIG. 6 is a diagram showing an example of an organ label conversion list that is comprised in the report generation unit.

FIG. 8 is a diagram illustrating a disease label conversion list.

FIG. 10 is a functional block diagram illustrating a learning model, an error acquisition unit, and a learning control unit.

FIG. 15 is a diagram conceptually showing the anatomical knowledge graph in the X-ray CT image.

FIG. 16 is a diagram conceptually showing the anatomical knowledge graph in the X-ray CT image.

FIG. 17 is a diagram conceptually showing the anatomical knowledge graph in a simple X-ray image.

FIG. 18 is a diagram showing an example of conversion of a disease knowledge graph comprised in the report generation unit.

FIG. 21 is a diagram illustrating learning of the learning model.

FIG. 23 is a diagram illustrating learning of the learning model.

DESCRIPTION OF THE PREFERRED EMBODIMENTS

Hereinafter, a preferred embodiment of a learning apparatus, a learning method, a trained model, and a program according to an embodiment of the present invention will be described with reference to accompanying drawings.

Figure 1:
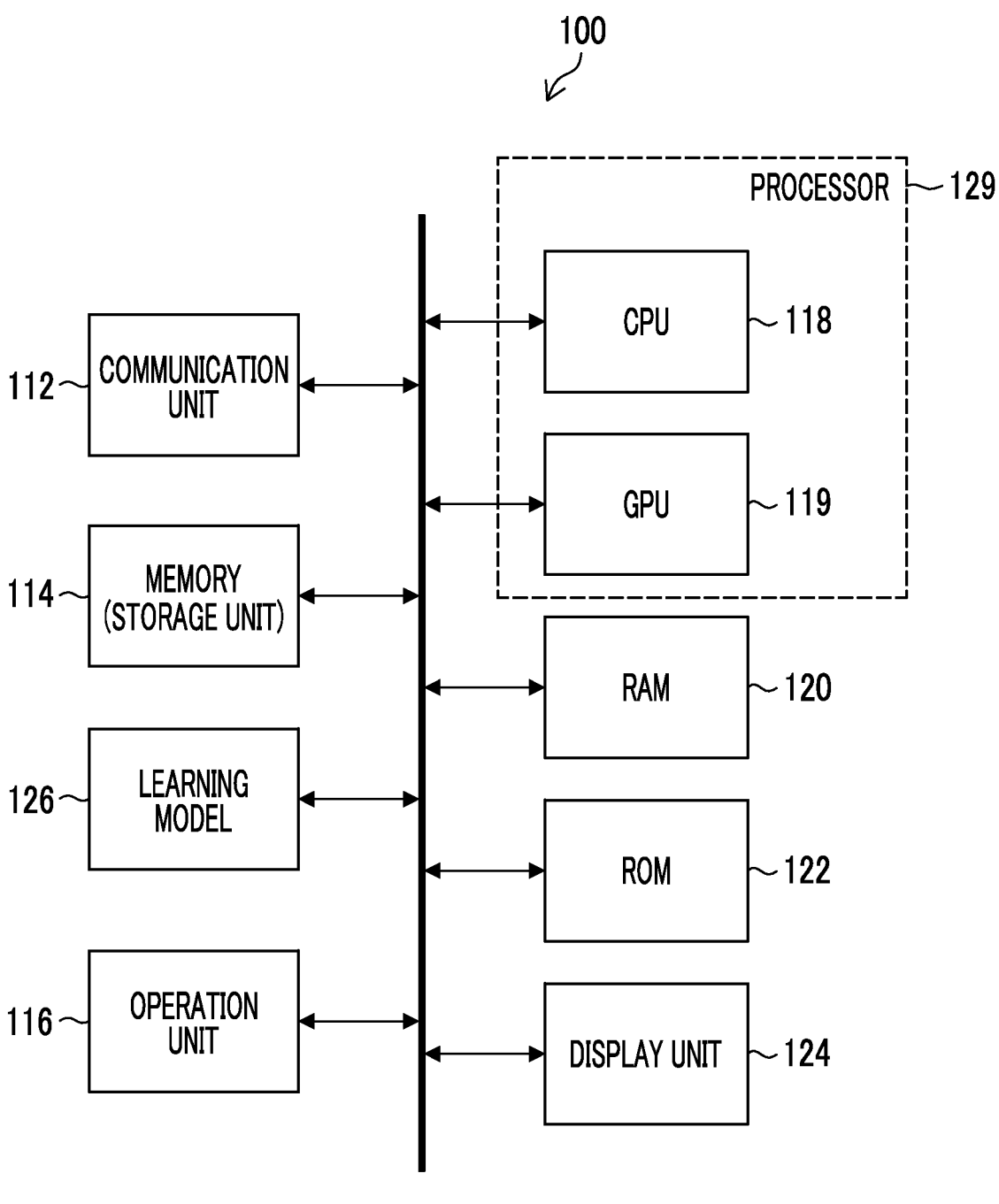
FIG. 1 is a block diagram showing an embodiment of a hardware configuration of a learning apparatus.

FIG. 1 is a block diagram showing an embodiment of a hardware configuration of a learning apparatus.

A learning apparatus 100 shown in FIG. 1 is configured by a computer. The computer may be a personal computer, a workstation, or a server computer. The learning apparatus 100 comprises a communication unit 112, a memory (storage unit) 114, a learning model 126, an operation unit 116, a central processing unit (CPU) 118, a graphics processing unit (GPU) 119, a random access memory (RAM) 120, a read only memory (ROM) 122, and a display unit 124. Note that, CPU 118 and GPU 119 constitute a processor 129. Further, the GPU 119 may be omitted in the processor 129.

The communication unit 112 is an interface that performs communication processing with an external device in a wired or wireless manner and performs exchange of information with the external device.

The memory 114 is configured to include, for example, a hard disk device, an optical disk, a magneto-optical disk, a semiconductor memory, or a storage device configured by using an appropriate combination thereof. The memory 114 stores various programs, data, and the like necessary for image processing such as learning processing and/or image generation processing. The program stored in the memory 114 is loaded into the RAM 120, and the processor 129 executes the program, so that the computer functions as means for performing various pieces of processing defined by the program. A training data set described below is also stored in the memory.

The operation unit 116 is an input interface that receives various operation inputs with respect to the learning apparatus 100. The operation unit 116 may be, for example, a keyboard, a mouse, a touch panel, an operation button, a voice input device, or an appropriate combination thereof.

The processor 129 reads out various programs stored in the ROM 122, the memory 114, or the like, and executes various pieces of processing. The RAM 120 is used as a work area of the processor 129. Further, the RAM 120 is used as a storage unit that temporarily stores the read-out program and various types of data.

The display unit 124 is an output interface on which various types of information are displayed. The display unit 124 may be, for example, a liquid crystal display, an organic electro-luminescence (OEL) display, a projector, or an appropriate combination thereof.

The learning model 126 is configured of a convolutional neural network (CNN). In the learning model 126, as described below, a pseudo simple X-ray image generated from an X-ray CT image is input, and an interpretation report is generated on the basis of the input pseudo simple X-ray image. The learning model 126 in the learning apparatus 100 has not been trained, and the learning apparatus 100 according to the embodiment of the present invention causes the learning model 126 to perform machine learning.

First Embodiment

A first embodiment will be described. In the following description, learning of a learning model that generates a pseudo simple X-ray image from an X-ray CT image having three dimensional information obtained by imaging a chest and outputs an interpretation report of the pseudo simple X-ray image will be described.

Figure 2:
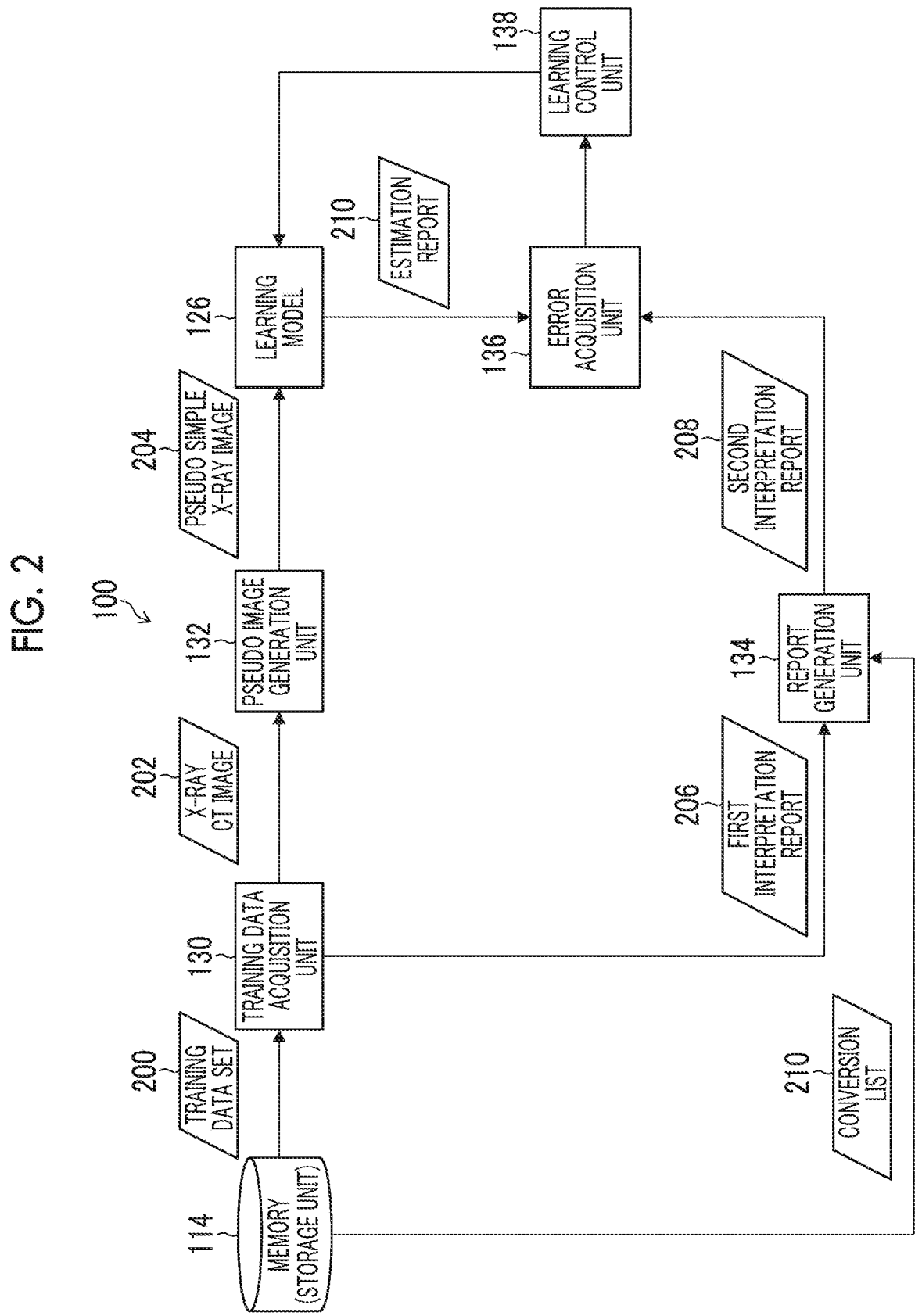
FIG. 2 is a block diagram illustrating a main function of the learning apparatus.

FIG. 2 is a block diagram illustrating a main function of the learning apparatus 100 according to the present embodiment.

The learning apparatus 100 mainly includes the memory 114, the processor 129, and the learning model 126 (see FIG. 1). The processor 129 realizes functions of a training data acquisition unit 130, a pseudo image generation unit 132, a report generation unit 134, an error acquisition unit 136, and a learning control unit 138.

The training data acquisition unit 130 acquires a training data set used for learning that is stored in the memory 114. For example, the training data set includes an X-ray CT image obtained by imaging a chest of a patient and a first interpretation report with respect to the X-ray image. The first interpretation report is a report created by a doctor or the like through interpretation of the X-ray CT image.

FIG. 3 is a diagram illustrating an X-ray CT image and a first interpretation report 206, which are an example of the training data set.

The training data set 200 includes a set of an X-ray CT image 202 and the first interpretation report 206. The memory 114 stores a plurality of training data sets 200, and learning of the learning model 126 is performed by using the plurality of training data sets 200.

The X-ray CT image 202 is obtained by actually imaging the patient as a subject. The X-ray CT image 202 has three dimensional information (three dimensional space information). Therefore, in a case in which the interpretation report (first interpretation report 206) is generated on the basis of the X-ray CT image 202, the doctor can observe an organ or the like on the basis of the three dimensional information. Therefore, the doctor can create an interpretation report in more detail and with higher accuracy in a case in which the interpretation report is created on the basis of the X-ray CT image 202 having three dimensional information than in a case in which the interpretation report is created on the basis of the simple X-ray image having two dimensional information. In the X-ray CT image 202, cross-sections 600S, 600C, and 600A are cross-sections in a sagittal direction, a coronal direction, and an axial direction, respectively. In addition, the illustrated X-ray CT image 202 obtained by imaging the chest is an example of the X-ray CT image, and X-ray CT images obtained by imaging other parts are also used in the present embodiment.

The first interpretation report 206 has information interpreted from the X-ray CT image 202. The first interpretation report 206 has anatomical structure information that can be interpreted from the X-ray CT image 202. Since the X-ray CT image 202 has the three dimensional information, the doctor can observe, for example, a lung by dividing the lung into finer areas. Therefore, the first interpretation report 206 states that "An irregular solid tumor is recognized in right areas S4 and S5".

The first interpretation report 206 has a disease label that can be interpreted from the X-ray CT image 202. Since the X-ray CT image 202 has the three dimensional information, the doctor can observe, for example, a shape of a margin in more detail. Therefore, the first interpretation report 206 states that "The margin is serrated with spicules, and a pleural invagination is also recognized".

The training data acquisition unit 130 acquires the training data set 200 from the memory 114, transmits the X-ray CT image 202 to the pseudo image generation unit 132, and transmits the first interpretation report 206 to the report generation unit 134.

Figure 4:
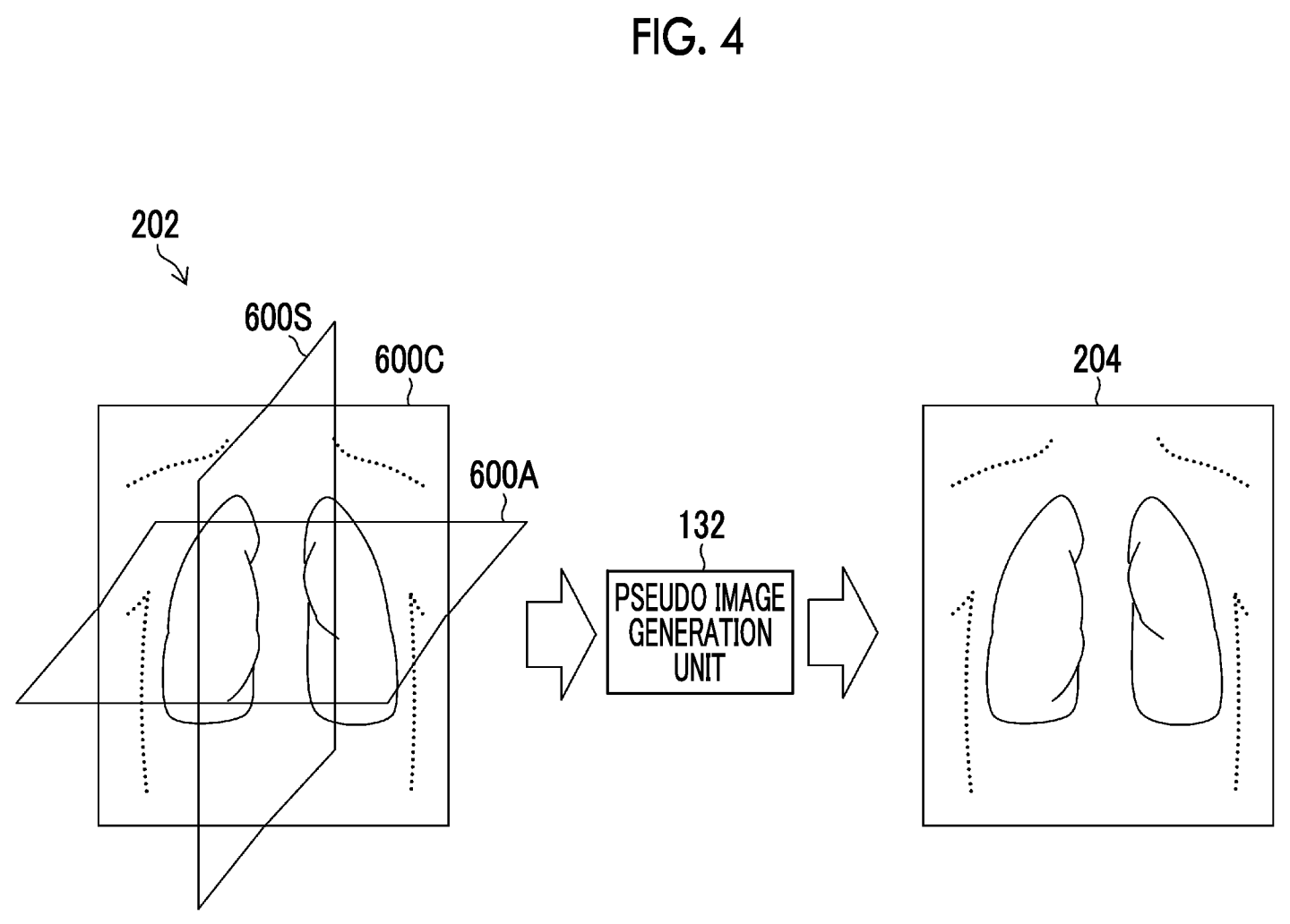

FIG. 4 is a diagram illustrating the pseudo image generation unit 132.

The pseudo image generation unit 132 generates a pseudo simple X-ray image 204 having two dimensional information from the input X-ray CT image 202 having three dimensional information. The pseudo image generation unit 132 can generate the pseudo simple X-ray image 204 from the X-ray CT image 202 by various methods. For example, the pseudo image generation unit 132 generates the pseudo simple X-ray image 204 from the X-ray CT image 202 by a post-digitally reconstructed radiograph (DRR) method described in a document "A method to produce and validate a digitally reconstructed radiograph-based computer simulation for optimisation of chest radiographs acquired with a computed radiography imaging system, C S MOORE, The British Journal of Radiology, 84 (2011), 890-902".

FIG. 5 is a diagram illustrating the report generation unit 134.

The report generation unit 134 generates a second interpretation report 208 on the basis of the input first interpretation report 206. The report generation unit 134 can generate the second interpretation report 208 from the first interpretation report 206 by various methods. For example, the report generation unit 134 comprises a conversion list, and generates the second interpretation report 208 by converting a text stated in the first interpretation report 206 on the basis of the conversion list. Specifically, the report generation unit 134 comprises an organ label conversion list 205A (FIG. 6), and generates the second interpretation report from the first interpretation report by converting an organ label used in the first interpretation report 206 into an organ label of the second interpretation report 208. Further, the report generation unit 134 comprises a disease label conversion list 205B (FIG. 8), and generates the second interpretation report from the first interpretation report 206 by converting a disease label used in the first interpretation report 206 into a disease label of the second interpretation report 208. The organ label conversion list 205A and the disease label conversion list 205B are specific examples, and the report generation unit 134 may comprise another conversion list and generate the second interpretation report 208 from the first interpretation report 206 using the other conversion list.

FIG. 6 is a diagram showing an example of the organ label conversion list 205A that is comprised in the report generation unit 134. In FIG. 6, the organ label conversion list of a right lung is shown, and the organ label conversion list of a left lung is not shown.

As shown in the organ label conversion list 205A, each of the three dimensional organ labels in the right lung is converted into a two dimensional organ label. Specifically, areas S1 to S3 of the right lung in the three dimensional organ label are converted into a right upper lung T1 in the two dimensional organ label. In addition, right areas S4 to S6 are converted into a right lower lung T3 in the two dimensional organ label. Further, areas S7 to S10 are converted into a right middle lung T2 in the two dimensional organ label. Here, the three dimensional organ label is segmented into relatively fine areas on the basis of the X-ray CT image 202 having three dimensional information. On the other hand, the two dimensional organ label corresponds to the simple X-ray image having two dimensional information and is relatively roughly segmented. A correspondence relationship between the three dimensional organ label and the two dimensional organ label will be described below.

Figure 7:
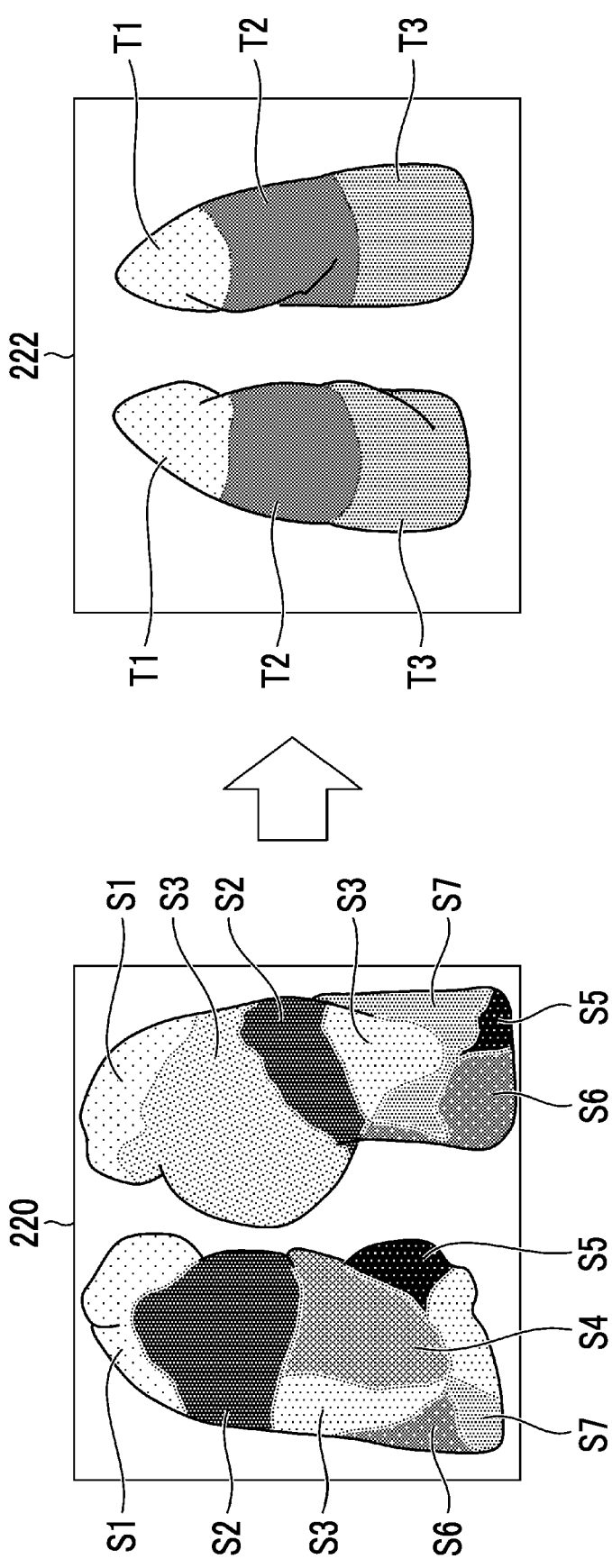
FIG. 7 is a diagram illustrating a correspondence relationship between a three dimensional organ label and a two dimensional organ label.

FIG. 7 is a diagram illustrating the correspondence relationship between the three dimensional organ label and the two dimensional organ label.

An organ label 220 is attached according to the anatomical structure information obtained from the X-ray CT image 202. Since the X-ray CT image 202 has the three dimensional information of the organ, labels are assigned to ten areas (area S1 to area S10) of each of the left and right lungs as illustrated. Since the X-ray CT image 202 has the three dimensional information of the lung, a front side and a back side of the lung can be observed. Therefore, the lung can be segmented into fine areas and labeled.

On the other hand, since the simple X-ray image has the two dimensional information, an organ label 222 is attached. In the simple X-ray image, labels are assigned to three areas (upper lung T1, middle lung T2, and lower lung T3) of each of the left and right lungs as illustrated. Since the simple X-ray image has no three dimensional information of the lung, the front side and the back side of the lung cannot be observed. Therefore, the lung can be segmented into three areas and labeled. Method of providing the lung areas in the X-ray CT image 202 and the simple X-ray image described above is an example, and the lung areas may be provided in other forms. In this way, the report generation unit 134 generates the second interpretation report 208 from the first interpretation report 206 by using the organ label conversion list 205A.

FIG. 8 is a diagram illustrating the disease label conversion list 205B that is comprised in the report generation unit 134.

As shown in the illustrated disease label conversion list 205B, each of three dimensional disease labels is converted into a two dimensional disease label. Specifically, a spicule, a serration, and a lobulation in the three dimensional disease label are converted to an irregular shape in the two dimensional disease label. In addition, a calcification of the three dimensional disease label is converted into "oo" in the two dimensional disease label. Further, a cavity of the three dimensional disease label is converted into "xx" in the two dimensional disease label. Here, a relatively detailed disease label is assigned to the three dimensional disease label on the basis of the X-ray CT image 202 having three dimensional information. On the other hand, the two dimensional disease label corresponds to the simple X-ray image having two dimensional information, and a relatively rough disease label is assigned. The disease label of the lung in the X-ray CT image 202 and the simple X-ray image described above is an example, and the disease label of the lung may be assigned in other forms. In this way, the report generation unit 134 generates the second interpretation report 208 from the first interpretation report 206 by using the disease label conversion list 205B.

Figure 9:
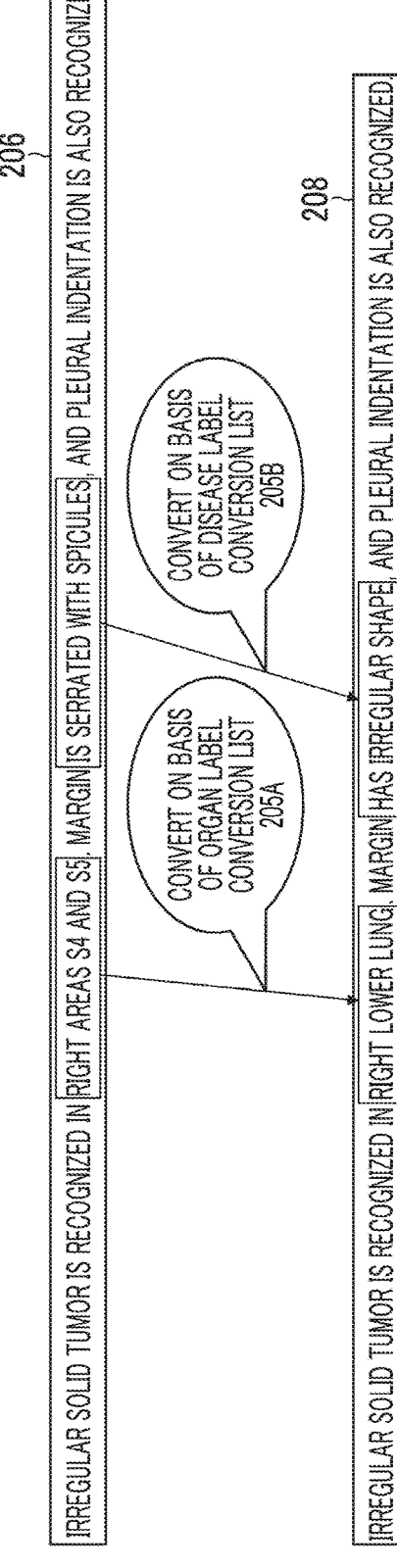
FIG. 9 is a diagram illustrating conversion from a first report into a second report in the report generation unit.

FIG. 9 is a diagram illustrating conversion from the first report into the second report in the report generation unit 134 comprising the organ label conversion list 205A and the disease label conversion list 205B described above.

As illustrated, the report generation unit 134 converts "right areas S4 and S5" of the first interpretation report 206 into "right lower lung" on the basis of the organ label conversion list 205A to generate the second interpretation report 208. In addition, the report generation unit 134 generates the second interpretation report 208 by converting "is serrated with spicules" of the first interpretation report 206 into "has an irregular shape" on the basis of the disease label conversion list 205B.

As described above, the report generation unit 134 comprises the conversion list, and generates the second interpretation report 208 from the first interpretation report 206 on the basis of the conversion list. In the above description, an example in which the report generation unit 134 generates the second interpretation report 208 from the first interpretation report 206 by using the conversion list is described, but the present embodiment is not limited thereto. For example, the report generation unit 134 may be configured by a trained model and generate the second interpretation report 208 from the first interpretation report 206.

Figure 10:
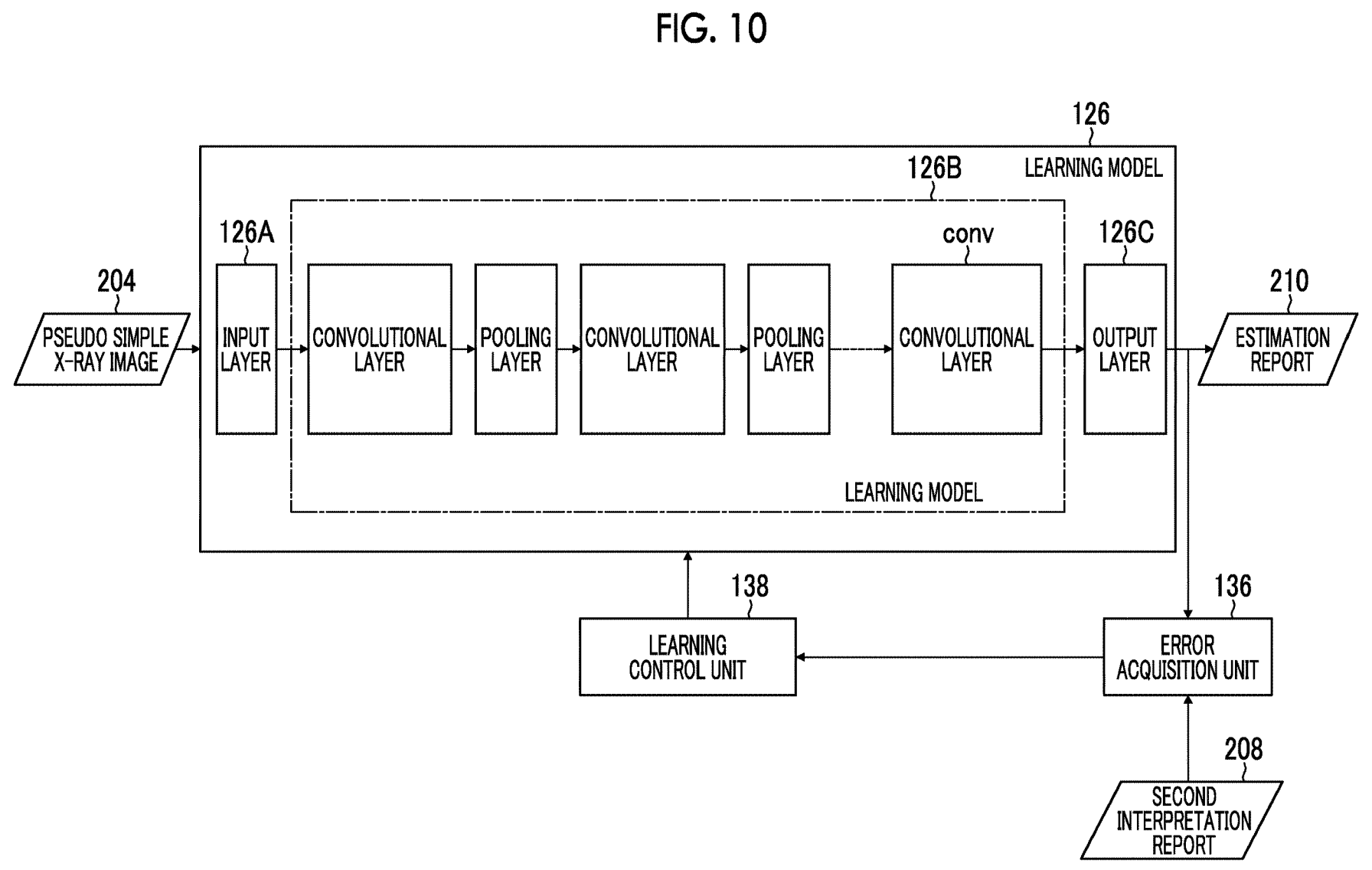

FIG. 10 is a functional block diagram illustrating the learning model 126, the error acquisition unit 136, and the learning control unit 138.

The learning model 126 is configured of a convolutional neural network (CNN) that is one of deep learning models.

The learning model 126 has a plurality of layer structures and holds a plurality of weight parameters. The learning model 126 can change from an untrained model to a trained model by updating the weight parameter from an initial value to an optimum value. The initial value of the weight parameter of the learning model 126 may be a random value or, for example, a weight parameter of a trained model that outputs a known interpretation report may be applied.

The learning model 126 comprises an input layer 126A, an intermediate layer 126B having a plurality of sets of a convolutional layer and a pooling layer, and an output layer 126C, and each layer has a structure in which a plurality of "nodes" are connected by "edges".

The pseudo simple X-ray image 204 of the training data set 200 is input to the input layer 126A.

The intermediate layer 126B has a convolutional layer, a pooling layer, and the like, and is a portion that extracts a feature from an image input from the input layer 126A. The convolutional layer acquires a "feature map" by performing filter processing (performing a convolution operation using a filter) on a nearby node in the previous layer. The pooling layer reduces the feature map output from the convolutional layer to obtain a new feature map. The "convolutional layer" plays a role of performing feature extraction such as edge extraction from the image, and the "pooling layer" plays a role of giving robustness such that the extracted feature is not affected by translation or the like. The intermediate layer 126B is not limited to a case in which the convolutional layer and the pooling layer are alternately disposed, and includes a case in which the convolutional layers are continuous, and a normalization layer. The convolutional layer cony in the final stage is a portion that outputs a feature map indicating an event interpreted from the pseudo simple X-ray image 204.

The output layer 126C is a portion that outputs an output result (estimation report 210) of the learning model 126.

The error acquisition unit 136 acquires the output result (estimation report 210) output from the output layer 126C of the learning model 126 and the second interpretation report 208 corresponding to the pseudo simple X-ray image 204, and calculates an error between the two. As a method of calculating the error, for example, Jaccard coefficient or Dice coefficient may be used.

The learning control unit 138 adjusts the weight parameter of the learning model 126 by the error backpropagation method based on the error calculated by the error acquisition unit 136 in order to minimize a distance or maximize a similarity in the feature amount space between the second interpretation report 208 and the output of the learning model 126.

This parameter adjustment processing is repeatedly performed, and learning is repeatedly performed until the error calculated by the error acquisition unit 136 converges.

In this way, the trained learning model 126 in which the weight parameter is optimized is created by using the training data set.

Next, a learning method using the learning apparatus 100 will be described.

Figure 11:
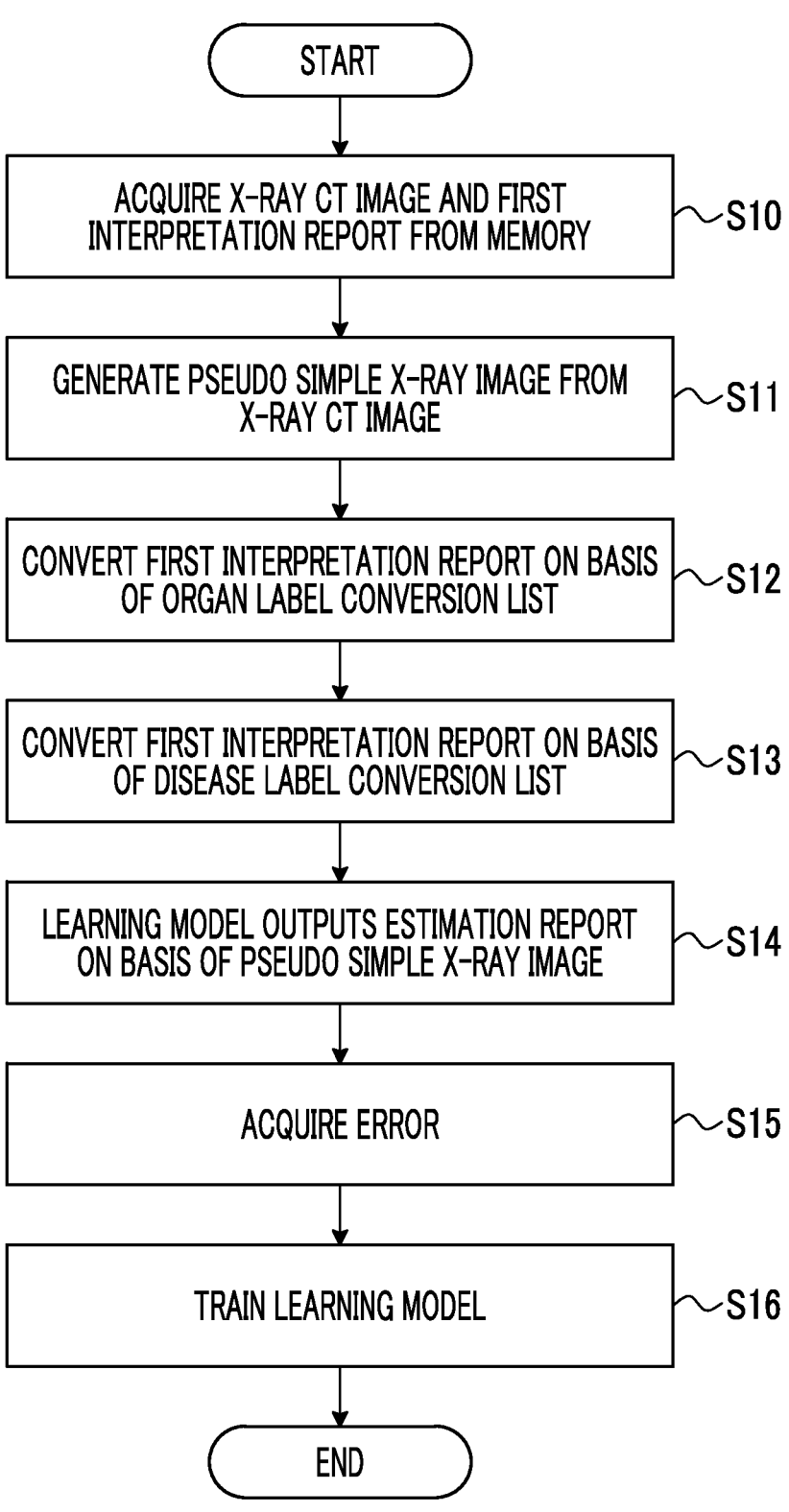
FIG. 11 is a flowchart illustrating a learning method using the learning apparatus and each step executed by the processor according to a program.

FIG. 11 is a flowchart illustrating a learning method using the learning apparatus 100 and each step executed by the processor according to a learning program.

First, the training data acquisition unit 130 acquires the training data set (the X-ray CT image 202 and the first interpretation report 206) 200 stored in the memory 114 (step S10). Thereafter, the X-ray CT image 202 is transmitted to the pseudo image generation unit 132, and the pseudo image generation unit 132 generates the pseudo simple X-ray image 204 on the basis of the X-ray CT image 202 (step S11). Next, the report generation unit 134 converts the organ label 220 of the first interpretation report 206 on the basis of the organ label conversion list 205A (step S12). The report generation unit 134 converts the disease label of the first interpretation report 206 on the basis of the disease label conversion list (step S13). With the conversion of the label, the report generation unit 134 generates the second interpretation report 208. Next, the learning model 126 outputs the estimation report 210 on the basis of the input pseudo simple X-ray image 204 (step S14). Thereafter, the error acquisition unit 136 acquires the error between the estimation report 210 and the second interpretation report 208 (step S15), and the learning control unit 138 trains the learning model 126 on the basis of the acquired error (step S16).

As described above, according to the present embodiment, the pseudo simple X-ray image 204 and the second interpretation report 208 with respect to the pseudo simple X-ray image 204 are generated from the training data set 200 of the X-ray CT image 202 having three dimensional information and the first interpretation report 206 with respect to the X-ray CT image 202, and learning is performed by using the pseudo simple X-ray image 204 and the second interpretation report 208. As a result, in the present embodiment, learning can be performed such that an interpretation report with high accuracy is output. With the trained model trained by the learning method according to the present embodiment, the simple X-ray image is input, and an interpretation report with high accuracy of the input simple X-ray image can be output.

Second Embodiment

In the example described above, the example in which the supine pseudo simple X-ray image 204 is generated from the standing X-ray CT image 202 has been described. However, in the present embodiment, even in a case in which the supine X-ray CT image 202 (first posture) is stored in the memory 114, the standing pseudo simple X-ray image 204 (second posture) can be generated and input to the learning model 126.

Figure 12:
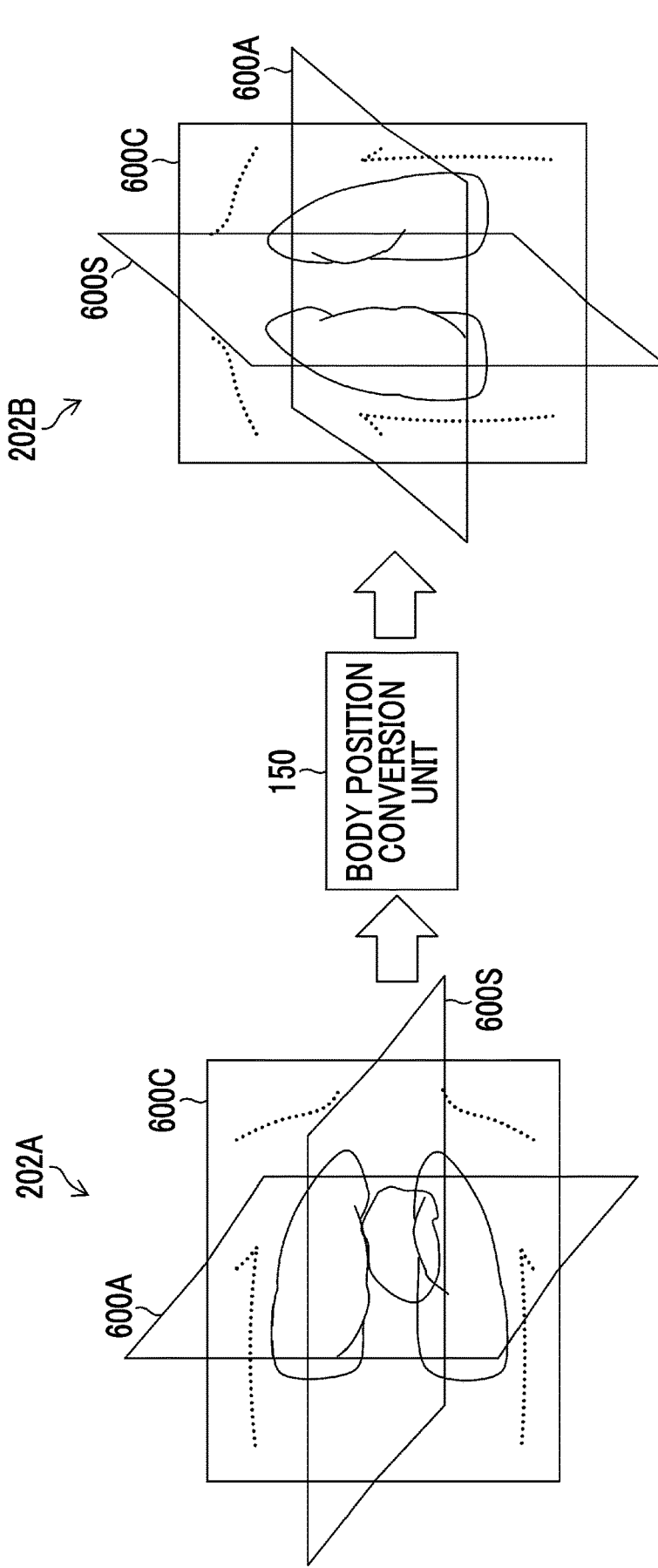
FIG. 12 is a diagram illustrating a body position conversion unit that converts a supine X-ray CT image into a standing X-ray CT image.

FIG. 12 is a diagram illustrating a body position conversion unit 150 that converts a supine X-ray CT image into a standing X-ray CT image. Note that the body position conversion unit 150 is comprised in the training data acquisition unit 130, for example.

The body position conversion unit 150 converts a supine X-ray CT image 202A stored in the memory 114 into a standing X-ray CT image. The body position conversion unit 150 can convert the supine X-ray CT image 202A into a standing X-ray CT image 202B by various methods. For example, the body position conversion unit 150 may be configured by a trained model obtained by machine learning, and may output the standing X-ray CT image 202B from the input supine X-ray CT image 202A.

As described above, in the present embodiment, the supine X-ray CT image 202A is converted into the standing X-ray CT image 202B. Then, the pseudo image generation unit 132 generates the pseudo simple X-ray image 204 from the converted standing X-ray CT image 202B. Therefore, an X-ray CT image captured in a supine position can also be appropriately used in the present embodiment.

Third Embodiment

In the example described above, the example in which the estimation report 210 is generated on the basis of the pseudo simple X-ray image 204 of an AP (from anterior to posterior) image or a PA image (from posterior to anterior) on the basis of the X-ray CT image 202 has been described. However, in the present embodiment, a captured pseudo X-ray image is generated from an image in another direction, for example, a lateral image, and the estimation report 210 is generated on the basis of the pseudo X-ray image.

Figure 13:
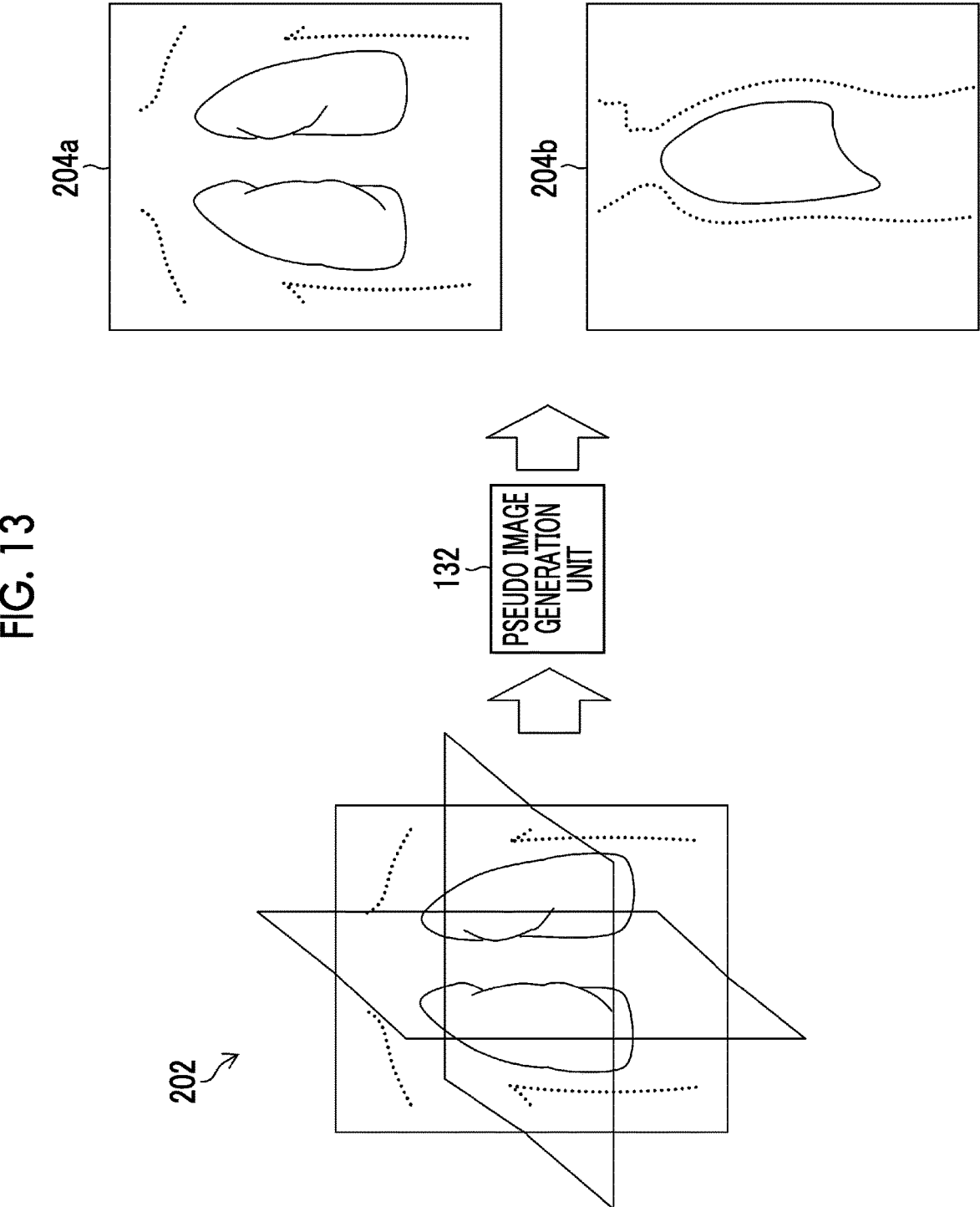
FIG. 13 is a diagram illustrating that the pseudo image generation unit generates pseudo X-ray images in two directions.

FIG. 13 is a diagram illustrating that the pseudo image generation unit 132 generates the pseudo X-ray images in two directions.

The pseudo image generation unit 132 generates a pseudo simple X-ray image 204*a* projected in an AP direction (first direction) and a pseudo simple X-ray image 204*b* projected in a lateral (LAT) direction (second direction) on the basis of the X-ray CT image 202. The pseudo image generation unit 132 can generate the pseudo simple X-ray image 204*a* in the AP direction and the pseudo simple X-ray image 204*b* in the LAT direction by a known technique. For example, the pseudo image generation unit 132 generates the pseudo simple X-ray image 204*a* in the AP direction and the pseudo simple X-ray image 204*b* in the LAT direction by the above-described DRR method.

As described above, in the present embodiment, the pseudo simple X-ray image 204*a* projected in the AP direction and the pseudo simple X-ray image 204*b* projected in the LAT direction are generated on the basis of the X-ray CT image 202. Then, since the pseudo simple X-ray image 204*a* projected in the AP direction and the pseudo simple X-ray image 204*b* projected in the LAT direction are input to the learning model 126, learning is performed such that an interpretation report with higher accuracy is output.

Fourth Embodiment

In the example described above, the example in which the report generation unit 134 comprises the organ label conversion list 205A and the disease label conversion list 205B has been described. In the present embodiment, the report generation unit 134 converts a knowledge graph, and generates the second interpretation report 208 from the first interpretation report 206 on the basis of the conversion. Specifically, the report generation unit 134 converts a first knowledge graph corresponding to the first interpretation report 206 into a second knowledge graph corresponding to the second interpretation report 208, and generates the estimation report 210 on the basis of the conversion. For example, the report generation unit 134 comprises an anatomical knowledge graph for an X-ray CT image (first knowledge graph) and a disease knowledge graph for an X-ray CT image (first knowledge graph), and converts the knowledge graphs into an anatomical knowledge graph for a simple X-ray image (second knowledge graph) and a disease knowledge graph for a simple X-ray image (second knowledge graph), respectively. Then, the report generation unit 134 generates the second interpretation report on the basis of the conversion.

Figure 14:
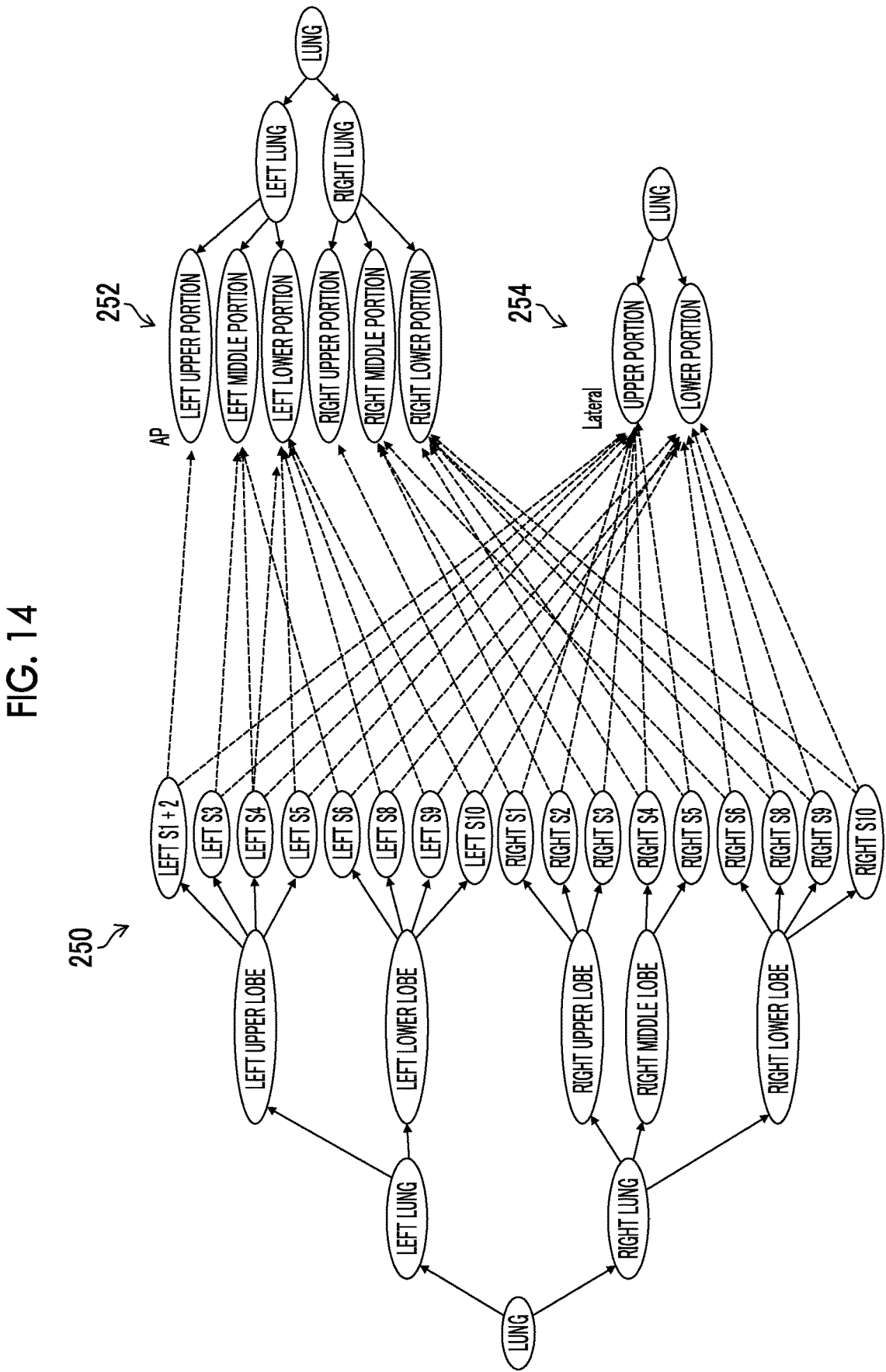
FIG. 14 is a diagram illustrating an example of conversion of an anatomical knowledge graph comprised in the report generation unit.

FIG. 14 is a diagram illustrating an example of the conversion of the anatomical knowledge graph comprised in the report generation unit 134.

In FIG. 14, a reference numeral 250 indicates the anatomical knowledge graph for an X-ray CT image. Since the X-ray CT image 202 has the three dimensional information, the areas of the lung can be more finely segmented.

FIGS. 15 and 16 are diagrams conceptually showing the anatomical knowledge graph in the X-ray CT image 202. FIG. 15 is a diagram showing areas in a case of being viewed from an inner side of the lung, and FIG. 16 is a diagram showing areas in a case of being viewed from an outer side of the lung.

An area of the right lung is indicated by a reference numeral 260 in FIG. 15 and a reference numeral 264 in FIG. 16. The right lung is segmented into ten areas of S1 to S10. Note that the S4 area is shown in FIG. 16 because the S4 area cannot be observed from the inner side. On the other hand, an area of the left lung is indicated by a reference numeral 262 in FIG. 15 and a reference numeral 266 in FIG. 16. The left lung is segmented into S1 to S10 areas in the same manner as the right lung, but is segmented into nine areas because S1 and S2 are the same area (denoted as S1+2). As described above, since the X-ray CT image 202 has the three dimensional information, each of the right lung and the left lung can be segmented from the S1 area to the S10 area as described above.

In FIG. 14, anatomical knowledge graphs denoted by reference numerals 252 and 254 are for simple X-ray images (the AP image and the Lateral image). In the simple X-ray image, each of the right lung and the left lung is segmented into three areas in the AP image, and each lung is segmented into two areas in the Lateral image.

FIG. 17 is a diagram conceptually showing the anatomical knowledge graph in the simple X-ray image.

A right lung of a simple X-ray image 268*a* of the AP image is provided with areas of a right lung upper portion U1, a right lung middle portion U2, and a right lung lower portion U3, and a left lung is provided with areas of a left lung upper portion U4, a left lung middle portion U5, and a left lung lower portion U6. In addition, lungs of a simple X-ray image 268*b* of the Lateral image are provided with an upper portion U7 and a lower portion U8.

In the anatomical knowledge graph 250 for an X-ray CT image shown in FIG. 14, the lung branches into the right lung and the left lung, and the left lung branches into a left upper lobe and a left lower lobe. The left upper lobe branches into a left S1+S2 area, a left S3 area, a left S4 area, and a left S5 area. The left lower lobe branches into a left S6 area, a left S8 area, a left S9 area, and a left S10 area. The right lung branches into a right upper lobe, a right middle lobe, and a right lower lobe. The right upper lobe branches into a right S1 area, a right S2 area, and a right S3 area. The right middle lobe branches into a right S4 area and a right S5 area. The right lower lobe branches into a right S6 area, a right S8 area, a right S9 area, and a right S10 area.

In the anatomical knowledge graph for a simple X-ray image shown in FIG. 14, the anatomical knowledge graph of the simple X-ray image 268*a* of the AP image and the anatomical knowledge graph of the simple X-ray image 268*b* of the Lateral image are shown. In the anatomical knowledge graph of the simple X-ray image of the AP image, the lung is branched into the left lung and the right lung. The left lung is branched into a left upper portion, a left middle portion, and a left lower portion. In addition, the right lung is branched into a right upper portion, a right middle portion, and a right lower portion. In the anatomical knowledge graph of the simple X-ray image in a Lateral direction, the lung is branched into an upper portion and a lower portion. Then, the report generation unit 134 converts the anatomical knowledge graph 250 for an X-ray CT image into the anatomical knowledge graphs 252 and 254 for simple X-ray images as indicated by arrows in FIG. 14, and generates the second interpretation report 208 from the first interpretation report 206 on the basis of the conversion.

FIG. 18 is a diagram showing an example of conversion of the disease knowledge graph comprised in the report generation unit 134.

The disease knowledge graph shown in FIG. 18 is an example of a disease knowledge graph related to a nodule. In FIG. 18, data is described as a table because the data is complicated to describe as a knowledge graph.

A disease knowledge graph 270 for an X-ray CT image is divided into categories of absorption value, boundary, shape, marginal property, internal property, and relationship with surrounding tissue. A classification target (class) of the absorption value is classified into solid, partially solid, or ground-glass. The boundary is classified into clear and unclear. The shape is classified into an irregular shape and a circle-like shape. The marginal property is classified into irregular, smooth, serrated, specular, lobulated, and linear. The internal property is classified into air bronchogram, calcification, cavity, and fat. The relationship with the surrounding tissue is classified into pleural invagination and pleura contact.

On the other hand, in a disease knowledge graph 272 for a simple X-ray image, the absorption value is classified as only solid because the absorption value is not easily visually recognized due to an absorption coefficient similar to that of the lung tissue. The boundary is classified into clear and unclear as in the disease knowledge graph 270 for an X-ray CT image. The shape is also classified into an irregular shape and a circle-like shape as in the disease knowledge graph 270 for an X-ray CT image. Since only the overall shape can be visually recognized in the simple X-ray image, the marginal property is not described. The internal property is visually recognized due to the same absorption coefficient as bones, and is classified into calcification. The relationship with the surrounding tissue is classified into pleural invagination and pleural contact depending on an imaging direction. Then, the report generation unit 134 converts the disease knowledge graph 270 for an X-ray CT image into the disease knowledge graph 272 for a simple X-ray image as indicated by arrows in FIG. 18, and generates the second interpretation report 208 from the first interpretation report 206 on the basis of the conversion.

Figure 19:
FIG. 19 is a diagram illustrating conversion from the first report into the second report in the report generation unit comprising the anatomical knowledge graph and the disease knowledge graph.

FIG. 19 is a diagram illustrating conversion from the first report into the second report in the report generation unit 134 comprising the above-described anatomical knowledge graph and disease knowledge graph.

The report generation unit 134 converts "right areas S4 and S5" of the first interpretation report 280 into "right lower lung" on the basis of the conversion of the anatomical knowledge graph to generate the second interpretation report 282. In addition, the report generation unit 134 generates the second interpretation report 282 by deleting "The margin is serrated with spicules," of the first interpretation report 280 on the basis of the conversion of the disease knowledge graph.

As described above, in the present embodiment, the report generation unit 134 converts the anatomical knowledge graph and the disease knowledge graph from those for an X-ray CT image to those for a simple X-ray image, and generates the second interpretation report 282 from the first interpretation report 280 on the basis of the conversion.

Fifth Embodiment

First Example

Next, another embodiment (first example) of the learning of the learning model 126 will be described. In the above-described embodiment, an example in which the pseudo simple X-ray image 204 is input to the learning model 126 and learning is performed such that the error between the estimation report output from the learning model 126 and the second interpretation report is minimized has been described. In the example, learning of the learning model 126 is performed by using an actual X-ray image and a disease label of an actual X-ray image, which are additional training data set, in addition to the above-described learning.

Figure 20:
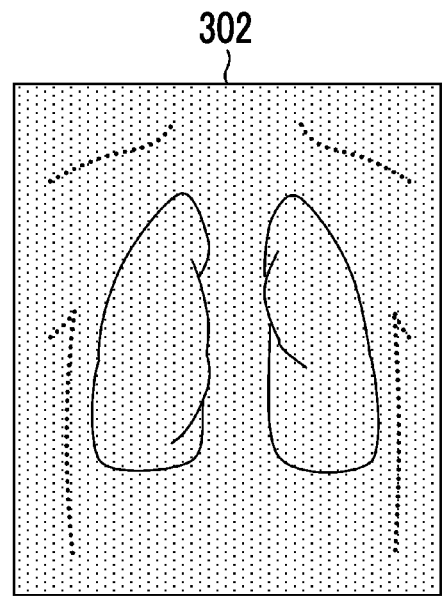
FIG. 20 is a diagram illustrating an additional training data set.

FIG. 20 is a diagram illustrating the additional training data set used in the example.

An additional training data set 300 includes an actual simple X-ray image 302 and a disease label 304. Here, the actual simple X-ray image 302 is an X-ray image obtained by actually imaging the chest in, for example, the AP direction. The disease label 304 is a label assigned by the doctor interpreting the actual simple X-ray image 302, and is, for example, a label indicating presence or absence of a nodule. Specifically, the additional training data set is acquired by national institutes of health (NIH) Chest X-ray Dataset or the like.

Figure 21:
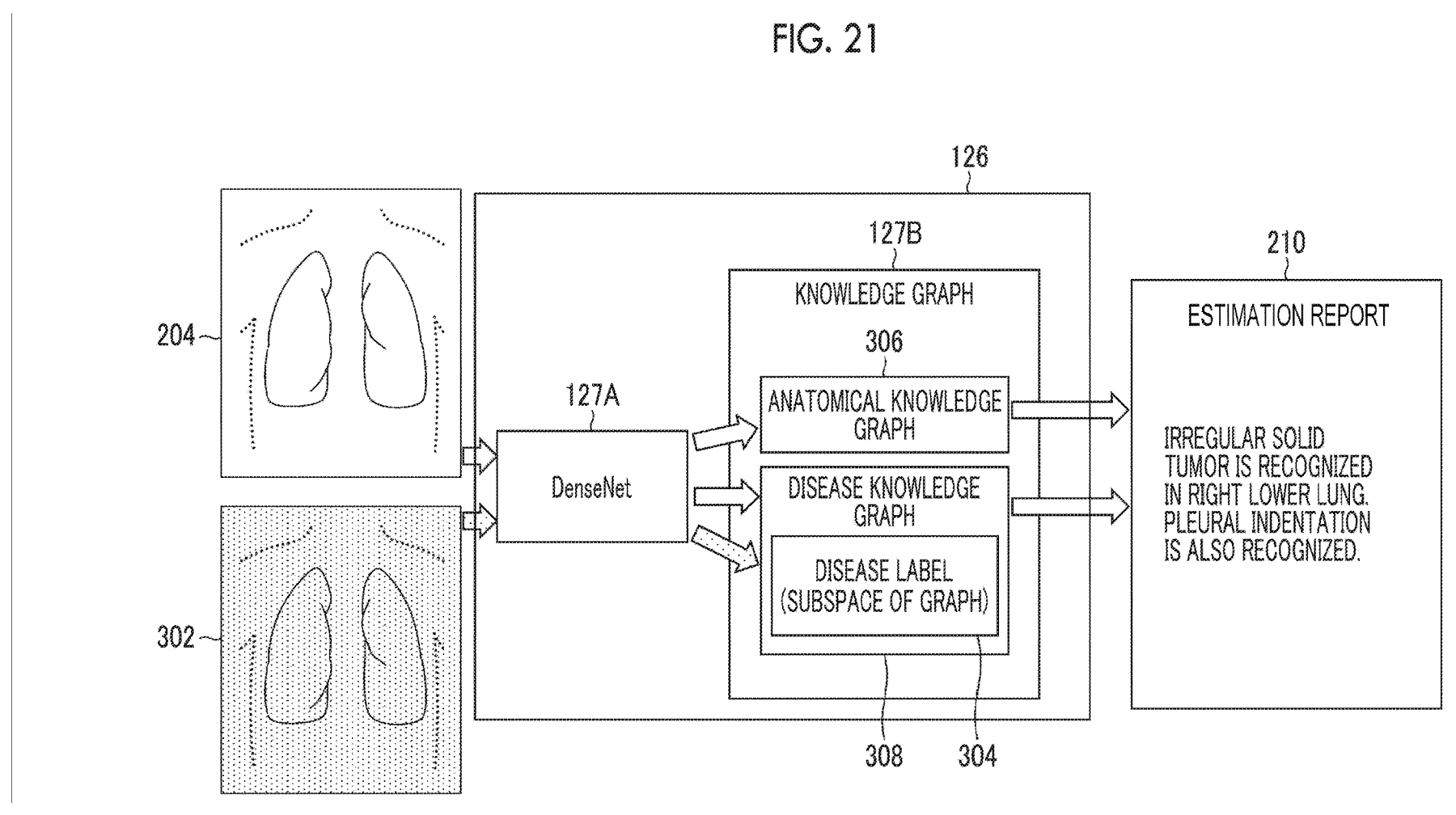

FIG. 21 is a diagram illustrating learning of the learning model 126 in the example.

In the example, the pseudo simple X-ray image 204 and the actual simple X-ray image 302 are input to the learning model 126. For example, the pseudo simple X-ray image 204 and the actual simple X-ray image 302 are alternately input to the learning model 126. Then, the learning model 126 outputs the estimation report 210. Here, the pseudo simple X-ray image 204 and the actual simple X-ray image 302 are images of the same subject, but may be images of different subjects.

The learning model 126 includes densely connected convolutional networks (DenseNet) 127A and a knowledge graph 127B. Here, the DenseNet 127A includes a plurality of dense blocks and a plurality of transition layers before and after the dense blocks, and has a network structure that exhibits high performances in the task of classification (for example, disease detection). The gradient vanishing is reduced by imposing skip connections on all layers in the dense blocks. As the transition layers, a convolutional layer and/or a pooling layer is provided. As a method of outputting an interpretation report from the knowledge graph 127B, for example, a technique described in a document "Li, Christy Y., et al. "Knowledge-driven encode, retrieve, paraphrase for medical image report generation.", AAAI, 2019" is used. The knowledge graph 127B outputs the estimation report 210 on the basis of an output from the DenseNet 127A. The knowledge graph 127B includes, for example, an anatomical knowledge graph 306 and a disease knowledge graph 308. Here, in learning of conversion from the pseudo X-ray image to the disease knowledge graph, assistance is performed by using the actual X-ray image and the disease label. Specifically, the disease label (presence or absence of a nodule) is added to a subspace of the knowledge graph 127B of the learning model 126, and the label of the presence or absence of a nodule is added to the errors in the actual X-ray image. As a result, the learning model 126 outputs the estimation report 210 with reference to the disease label 304, and learning is performed such that an interpretation report with higher accuracy is output.

Second Example

Next, another embodiment (second example) of the learning of the learning model 126 will be described. In the example, learning of the learning model 126 is performed by using an actual X-ray image and a disease label of an actual X-ray image, which are additional training data set, in addition to the above-described learning.

Figure 22:
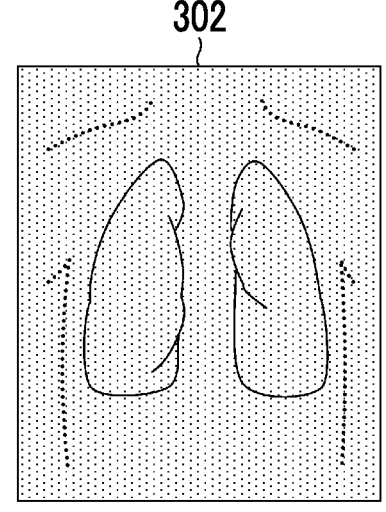
FIG. 22 is a diagram illustrating an additional training data set.

FIG. 22 is a diagram illustrating the additional training data set used in the example.

The additional training data set 320 includes the actual simple X-ray image 302 and an interpretation report (third interpretation report) 322. Here, the interpretation report 322 is, for example, an interpretation report created by a doctor by actually interpreting the actual simple X-ray image 302.

FIG. 23 is a diagram illustrating learning of the learning model 126 in the example. Parts already described will be denoted by the same reference numerals as described and the description thereof will be omitted.

In the example, the pseudo simple X-ray image 204 and the actual simple X-ray image 302 are input to the learning model 126. For example, the pseudo simple X-ray image 204 and the actual simple X-ray image 302 are alternately input to the learning model 126. Then, the learning model 126 outputs the estimation report 210 with respect to the pseudo simple X-ray image 204 and an estimation report 324 with respect to the actual simple X-ray image 302. Here, Learning is performed by using the same DenseNet 127A and the same knowledge graph 127B for the pseudo simple X-ray image 204 and the actual simple X-ray image 302. Specifically, in a case in which the pseudo simple X-ray image 204 is input, the estimation report 210 is output as described above, and the learning model 126 is trained using the error between the estimation report 210 and the second interpretation report. Meanwhile, in a case in which the actual simple X-ray image 302 is input, the estimation report 324 is output through the DenseNet 127A and the knowledge graph 127B as well. Then, the error acquisition unit 136 acquires an error between the output estimation report 324 and the interpretation report 322 of a part of the additional training data set 320, and the learning control unit 138 causes the learning model 126 to be trained on the basis of the error.

As described above, the learning model 126 performs learning using the actual simple X-ray image 302 in addition to learning using the pseudo simple X-ray image 204. With such learning, it is possible to generate a trained model that outputs an interpretation report with higher accuracy.

<Others>

In the above embodiment, the hardware structures of the processing units that execute various pieces of processing are various processors as follows. The various processors include: a central processing unit (CPU) that is a general-purpose processor functioning as various processing units by executing software (program); a programmable logic device (PLD) that is a processor of which circuit configuration can be changed after manufacture, such as a field programmable gate array (FPGA); a dedicated electrical circuit that is a processor having circuit configuration designed exclusively to execute specific processing, such as an application specific integrated circuit (ASIC); and the like.

One processing unit may be configured by one of these various processors, or may be configured by two or more processors of the same type or different types (for example, a plurality of FPGAs or a combination of a CPU and an FPGA). In addition, a plurality of processing units may be configured by one processor. As an example in which the plurality of processing units are configured by one processor, first, as represented by a computer, such as a client or a server, there is an aspect in which the one processor is configured by a combination of one or more CPUs and software and functions as the plurality of processing units. Second, as represented by a system on chip (SoC) or the like, there is an aspect in which a processor that realizes the functions of the entire system including the plurality of processing units with one integrated circuit (IC) chip is used. As described above, the various processing units are configured using one or more of the above-described various processors as hardware structures.

Further, the hardware structure of these various processors is more specifically an electric circuit (circuitry) in which circuit elements such as semiconductor elements are combined.

Each of the above-described configurations and functions can be appropriately realized by any hardware, software, or a combination of both. For example, the present invention can be applied to a program for causing a computer to execute the above-described processing steps (processing procedures), a computer-readable recording medium (non-transitory recording medium) on which such a program is recorded, or a computer on which such a program can be installed.

Although examples of the present invention have been described above, it goes without saying that the present invention is not limited to the above-described embodiments and various modifications may be made without departing from the scope of the present invention.

EXPLANATION OF REFERENCES

100: learning apparatus
112: communication unit
114: memory
116: operation unit
118: CPU
120: RAM
122: ROM
124: display unit
126: learning model
129: processor
130: training data acquisition unit
132: pseudo image generation unit
134: report generation unit
136: error acquisition unit
138: learning control unit
200: training data set
202: X-ray CT image
204: pseudo simple X-ray image
205A: organ label conversion list
205B: disease label conversion list
206: first interpretation report
208: second interpretation report
210: estimation report

What is claimed is:

1. A learning apparatus comprising:

a processor;

a memory that stores a training data set of an X-ray CT image having three dimensional information and a first interpretation report with respect to the X-ray CT image; and a learning model that generates an interpretation report from a simple X-ray image having two dimensional information, wherein the processor performs:

processing of acquiring a pseudo simple X-ray image, which is generated by projecting the X-ray CT image;

processing of generating a second interpretation report with respect to the pseudo simple X-ray image by converting the first interpretation report;

processing of inputting the pseudo simple X-ray image to the learning model and acquiring an estimation report with respect to the pseudo simple X-ray image;

processing of acquiring an error between the estimation report and the second interpretation report; and processing of training the learning model by using the error.

2. The learning apparatus according to claim 1, wherein in the processing of generating the second interpretation report, the second interpretation report is generated from the first interpretation report by converting an organ label included in the first interpretation report into an organ label of the second interpretation report.

3. The learning apparatus according to claim 1, wherein in the processing of generating the second interpretation report, the second interpretation report is generated from the first interpretation report by converting a disease label included in the first interpretation report into a disease label of the second interpretation report.

4. The learning apparatus according to claim 1, wherein in the processing of generating the second interpretation report, a first knowledge graph corresponding to the first interpretation report is converted into a second knowledge graph corresponding to the second interpretation report, and the second interpretation report is generated on the basis of the conversion.

5. The learning apparatus according to claim 1, wherein in a case in which the memory stores the X-ray CT image obtained by imaging a subject in a first posture and the learning model generates an interpretation report from the simple X-ray image obtained by imaging the subject in a second posture, in the processing of inputting the pseudo simple X-ray image, the pseudo simple X-ray image in the second posture is generated from the X-ray CT image in the first posture, and the pseudo simple X-ray image in the second posture is input to the learning model.

6. The learning apparatus according to claim 1, wherein in the processing of inputting the pseudo simple X-ray image, the pseudo simple X-ray image projected in a first direction and the pseudo simple X-ray image projected in a second direction are generated from the X-ray CT image, and the pseudo simple X-ray image projected in the first direction and the pseudo simple X-ray image projected in the second direction are input to the learning model.

7. The learning apparatus according to claim 1, wherein the memory stores an additional training data set of the simple X-ray image and a disease label of the simple X-ray image, and in the processing of acquiring the error, an error between the estimation report with respect to the pseudo simple X-ray image output by the learning model with reference to the disease label, and the second interpretation report is acquired.

8. The learning apparatus according to claim 1, wherein the memory stores an additional training data set of the simple X-ray image and a third interpretation report with respect to the simple X-ray image, and in the processing of acquiring the error, the error between the estimation report with respect to the pseudo simple X-ray image output by the learning model on the basis of the input pseudo simple X-ray image, and the second interpretation report and an error between an estimation report with respect to the simple X-ray image output by the learning model on the basis of the input simple X-ray image, and the third interpretation report are acquired.

9. The learning apparatus according to claim 1, wherein the processor generates the second interpretation report by converting a text stated in the first interpretation report on a basis of a predefined conversion list.

10. A learning method in which a processor trains a learning model, which generates an interpretation report from a simple X-ray image having two dimensional information, by using a training data set of an X-ray CT image having three dimensional information and a first interpretation report with respect to the X-ray CT image stored in a memory, the learning method comprising:

acquiring a pseudo simple X-ray image, which is generated by projecting the X-ray CT image;

generating a second interpretation report with respect to the pseudo simple X-ray image by converting the first interpretation report;

inputting the pseudo simple X-ray image to the learning model and acquiring an estimation report with respect to the pseudo simple X-ray image;

acquiring an error between the estimation report and the second interpretation report; and training the learning model by using the error.

11. The learning method according to claim 10, wherein the second interpretation report is generated from the first interpretation report by converting an organ label included in the first interpretation report into an organ label of the second interpretation report.

12. The learning method according to claim 10, wherein the second interpretation report is generated from the first interpretation report by converting a disease label included in the first interpretation report into a disease label of the second interpretation report.

13. The learning method according to claim 10, wherein a first knowledge graph corresponding to the first interpretation report is converted into a second knowledge graph corresponding to the second interpretation report, and the second interpretation report is generated on the basis of the conversion.

14. A non-transitory, computer-readable tangible recording medium on which a program for causing, when read by a computer, a processor of the computer to execute the learning method according to claim 10 is recorded.

15. A trained model trained by the learning method according to claim 10.

* * * * *